United States Patent [19]

Yaginuma et al.

[11] Patent Number: 5,574,150
[45] Date of Patent: Nov. 12, 1996

[54] EXCIPIENT HAVING HIGH COMPACTABILITY AND PROCESS FOR PREPARING SAME

[75] Inventors: Yoshihito Yaginuma; Sueo Nagatomo; Hiroto Miyamoto, all of Nobeoka, Japan

[73] Assignee: Asahi Kasei Kogyo Kabushiki Kaisha, Osaka, Japan

[21] Appl. No.: 176,623

[22] Filed: Jan. 3, 1994

[30] Foreign Application Priority Data

Jan. 5, 1993 [JP] Japan ................................ 5-000216

[51] Int. Cl.$^6$ .......................................... C08B 37/00
[52] U.S. Cl. ........................................ 536/56; 536/124
[58] Field of Search .............................. 536/56, 124

[56] References Cited

U.S. PATENT DOCUMENTS

| | | | |
|---|---|---|---|
| 2,978,446 | 4/1961 | Battista et al. | 536/56 |
| 3,141,875 | 7/1964 | Battista et al. | 536/56 |
| 3,146,168 | 8/1964 | Battista | 424/362 |
| 3,259,537 | 7/1966 | Battista | 536/56 |
| 3,278,519 | 10/1966 | Battista et al. | 536/56 |
| 3,345,357 | 10/1967 | Cruz, Jr. | 536/56 |
| 4,159,345 | 6/1979 | Takeo et al. | 424/362 |
| 4,302,111 | 11/1981 | Harris . | |
| 4,307,121 | 12/1981 | Thompson | 426/431 |
| 4,744,987 | 5/1988 | Mehra et al. | 514/781 |

FOREIGN PATENT DOCUMENTS

| | | |
|---|---|---|
| 699100 | 12/1964 | Canada . |
| 2387040 | 11/1978 | France . |
| 2921496A1 | 2/1980 | Germany . |
| 40-26274 | 11/1965 | Japan . |
| 51-17172 | 5/1976 | Japan . |
| 56-2047 | 1/1981 | Japan . |
| 56-38128 | 9/1981 | Japan . |
| 63-267731 | 11/1988 | Japan . |
| 1-272643 | 10/1989 | Japan . |
| 2-84401 | 3/1990 | Japan . |

OTHER PUBLICATIONS

Database WPI, Week 8628, Derwent Publications Ltd. (Inst. Celuloza Hirti) 30 Nov. 1985.
Battista et al. "Microcrystalline Cellulose" pp. 20–29 vol. 54, No. 9 Sep. 1962, Industrial and Engineering Chemistry.

Primary Examiner—Jeffrey C. Mullis
Attorney, Agent, or Firm—Pennie & Edmonds

[57] ABSTRACT

Disclosed is an excipient comprising white powdery microcrystalline cellulose having an average degree of polymerization of from 100 to 375 and an acetic acid holding capacity of 280% or more, and having a specific compression characteristic satisfying an equality of formula (1):

$$P \cdot \frac{V_o}{V_o - V_p} = \frac{1}{a \cdot b} + \frac{P}{a} \qquad (1)$$

wherein a is from 0.85 to 0.90, b is from 0.05 to 0.10, P represents the compression pressure (kgf/cm$^2$) applied to the microcrystalline cellulose, $V_o$ represents the apparent specific volume (cm$^3$/g) of the microcrystalline cellulose, and $V_p$ represents the specific volume (cm$^3$/g) of the microcrystalline cellulose at the compression pressure P. The excipient of the present invention exhibits not only high compactability but also high rate of disintegration. The excipient of the present invention can be advantageously obtained by heat-treating an aqueous dispersion of purified cellulose particles, which has a solids content of 40% or less by weight, at 100° C. or more, followed by drying, or by subjecting an aqueous dispersion of purified cellulose particles having a solids content of 23% or less by weight to thin film-forming treatment and drying the resultant thin film.

11 Claims, No Drawings

EXCIPIENT HAVING HIGH COMPACTABILITY AND PROCESS FOR PREPARING SAME

BACKGROUND OF THE INVENTION

1. Field of the Invention

The present invention relates to an excipient having high compactability and a process for preparing the same. More particularly, the present invention is concerned with an excipient having high compactability, comprising white powdery microcrystalline cellulose having an average degree of polymerization of from 100 to 375 and an acetic acid holding capacity of 280% or more, and having a specific compression characteristic. The present invention is also concerned with a process for preparing an excipient having high compactability, which comprises subjecting a cellulose material to hydrolysis with acid or oxidative degradation with alkali to form cellulose particles, subjecting the cellulose particles to purification to obtain aqueous purified cellulose particles, adjusting a water content of the aqueous purified cellulose particles to obtain an aqueous dispersion of the purified cellulose particles which has a solids content of 40% or less by weight, and subjecting the aqueous dispersion to heat treatment at 100° C. or more, followed by drying. Furthermore, the present invention is concerned with an alternative process for preparing an excipient having high compactability, which comprises subjecting an aqueous dispersion of the purified cellulose particles which has a solids content of 23% or less by weight to thin film-forming treatment to obtain a thin film of the aqueous dispersion, followed by drying.

2. Discussion of Related Art

It is known that powdery materials are compressed into a shaped product in order to not only improve the handling characteristics of the materials but also impart desired functions to the materials. The most important required property of the compressed shaped product (usually, tablet) is a strength such that the compression-shaped product is unlikely to suffer abrasion or destruction during transportation and use thereof. When the tablet is used as a pharmaceutical product, in addition to the above-mentioned requirement of strength, the disintegration time of the tablet must be short so that the tablet can express a prompt pharmacological effect after the tablet is orally taken. Generally, after orally taken, a tablet is disintegrated in digestive tracts and then a pharmaceutical ingredient is dissolved in a digestive liquid. The dissolved ingredient is absorbed through walls of the digestive tracts, and dissolved in blood. The blood having the ingredient dissolved therein is circulated in a body to thereby express a pharmacological effect. Therefore, when a tablet disintegrates in digestive tracts immediately after orally taken, a rapid expression of the pharmacological effect of the active ingredient contained in the tablet can be obtained.

Most of powdery materials as such can hardly be processed into a shaped form even by compression. Therefore, it is necessary to blend a powdery material with an excipient having compactability and subject the resultant mixture to compression. For imparting a desired strength to a shaped product (tablet), it is necessary to determine (1) an appropriate amount of the excipient and (2) an appropriate compression force for compaction. Generally, the more the amount of the excipient and the larger the compression force, the higher the strength of the resultant tablet.

However, when it is desired that the content of a main ingredient (powdery material) in a tablet be high, for example, when the size of a tablet is required to be small as in the pharmaceutical industry, the quantity of an excipient is necessarily limited. On the other hand, an excessive compression force causes a tableting machine to be heavily loaded, leading to a wear of parts of the machine. Furthermore, when a tablet is produced by mixing film-coated granules and an excipient and punching the resultant mixture (such a tablet is called a granule-containing tablet), or when an enzyme or antibiotic is fabricated into a tablet form, it is necessary to form a tablet with a small compression force so as to prevent a damage on the film and a deterioration of the enzyme or antibiotic. Therefore, in producing a tablet, it is desired to use an excipient capable of exhibiting a high compactability with a small amount thereof.

As a conventional excipient which is used for the above-mentioned purpose, microcrystalline cellulose is known. Since the microcrystalline cellulose exhibits high safety, a relatively high compactability and a relatively excellent rate of disintegration, it is widely used in the pharmaceutical industry.

With respect to the microcrystalline cellulose, it is known that when microcrystalline cellulose having an average degree of polymerization of from 15 to 375, a bulk of from 7 to 34 lb/ft$^3$ (1.84 to 8.92 cm$^3$/g) and an particle size of 300 μm or less is used for producing pharmaceutical tablets, the tablets have an increased strength and an improved rate of disintegration (U.S. Pat. No. 3,146,168 corresponding to Examined Japanese Patent Application Publication No. 40-26274). It is also known that when microcrystalline cellulose having an average degree of polymerization of from 60 to 375, an apparent specific volume of from 1.6 to 3.1 cm$^3$/g, a tapping apparent specific volume of 1.40 cm$^3$/g or more, a ratio of a 200-mesh sieve residue of from 2 to 80% by weight and a repose angle of 35° to 42° is mixed with a main ingredient or an additive, the resultant powder mix has high flowability, and tablets made therefrom have an increased rate of disintegration (U.S. Pat. No. 4,159,345 corresponding to Examined Japanese Patent Application Publication Nos. 56-2047 and 56-38128).

With respect to a cellulose powder having compactability, it is known that a cellulose powder having an average degree of polymerization of from about 450 to about 650, an apparent density of from 0.40 to 0.60 g/cm$^3$ (1.67 to 2.50 cm$^3$/g) in a compacted state and a ratio of a 200-mesh sieve residue of 50% or more by weight is suitable as excipient for forming tablets (Examined Japanese Patent Application Publication No. 51-17172). It is also known that a cellulose powder having a specific average diameter (30 μm or less) and a specific surface area (1.3 m$^2$/g or more) exhibits high compactability (Unexamined Japanese Patent Application Laid-Open Specification No. 63-267731), that a cellulose powder having a specific crystalline form (type I), a sum of respective volumes of pores having a diameter of 0.1 μm or more of 20% or more, based on the total apparent volume of the powder particles, and a ratio of a 350-mesh sieve residue of 90% or more by weight exhibits high flowability and compactability (Unexamined Japanese Patent Application Laid-Open Specification No. 1-272643), and that a cellulose powder having a crystalline form type I, a specific surface area of 20 m$^2$/g or more, a sum of respective volumes of pores having a diameter of 0.01 μm or more of 0.3 cm$^3$/g or more, and a ratio of particles having a diameter of 100 μm or less of 50% or more by weight exhibits high flowability and high compactability (Japanese Patent Application Laid-Open Specification No. 2-84401).

However, these conventional cellulose powders have a drawback in that the higher the compactability, the lower the rate of disintegration.

In general, for improving the compactability of a microcrystalline cellulose, it is effective to increase an apparent specific volume of the microcrystalline cellulose. For this purpose, attempts have been made to decrease the density of the microcrystalline cellulose particles by finely pulverizing microcrystalline cellulose (Unexamined Japanese Patent Application Laid-Open Specification No. 63-267731), or by rendering microcrystalline cellulose particles porous (Unexamined Japanese Patent Application Laid-Open Specification No. 2-84401). Since the product obtained in Unexamined Japanese Patent Application Laid-Open Specification No. 63-267731 is finely pulverized, the product naturally has a high apparent specific volume, and it has a low tapping apparent specific volume, so that it can be readily compacted to thereby give a tablet. However, a void space (water paths) within the tablet is decreased, so that the ability of the tablet to disintegrate is markedly deteriorated. On the other hand, the product obtained in Unexamined Japanese Patent Application Laid-Open Specification No. 2-84401 has extremely high specific surface area and high apparent specific volume because the particles of the microcrystalline cellulose have high porosity. However, such porous particles have a relatively low strength, so that the compression of the particles causes not only the particles to be adhered to one another, but also each particle to be deformed and become high in density. Therefore, the void space (water paths) within the tablet decreases, so that the ability of the tablet to disintegrate is markedly deteriorated.

As described above, conventional microcrystalline cellulose powders have drawbacks in that when the compactability of the microcrystalline cellulose powder is high, the rate of disintegration is low, whereas when the rate of disintegration is satisfactory, the compactability is low. That is, there is a serious technical dilemma.

Actually, although particularly in the pharmaceutical industry, an excipient is desired to have both a high compactability and an excellent rate of disintegration, excipients having a good balance of a compactability and a rate of disintegration have heretofore not been known.

SUMMARY OF THE INVENTION

In these situations, the present inventors have made extensive and intensive studies with a view toward developing microcrystalline cellulose having a good balance of a compactability and a rate of disintegration. As a result, it has been found that, with respect to an excipient comprising microcrystalline cellulose, a good balance of a compactability and a rate of integration can be achieved by providing a cellulose having an average degree of polymerization of from 100 to 375 and an acetic acid holding capacity of 280% or more, and having a compression characteristic satisfying an equality of formula (1):

$$P \cdot \frac{V_o}{V_o - V_p} = \frac{1}{a \cdot b} + \frac{P}{a} \qquad (1)$$

wherein a is from 0.85 to 0.90, b is from 0.05 to 0.10, P represents the compression pressure (kgf/cm$^2$) applied to the microcrystalline cellulose, $V_o$ represents the apparent specific volume (cm$^3$/g) of the microcrystalline cellulose, and $V_p$ represents the specific volume (cm$^3$/g) of the microcrystalline cellulose at the compression pressure P. It has also been found that an excipient comprising such new microcrystalline cellulose can be prepared by a process which comprises subjecting a cellulose material to hydrolysis with acid or oxidative degradation with alkali to form cellulose particles, subjecting the cellulose particles to purification to obtain aqueous purified cellulose particles, adjusting a water content of the aqueous purified cellulose particles to obtain an aqueous dispersion of the purified cellulose particles, wherein the aqueous dispersion has a solids content of 40% or less by weight, a pH value of from 5 to 8.5 and an electrical conductivity of 300 μS/cm or less, and subjecting the aqueous dispersion to heat treatment at 100° C. or more, followed by drying; or by a modification of the above process in which a water content of an aqueous dispersion of the purified cellulose particles is adjusted so that the aqueous dispersion has a solids content of 23% or less, a pH value of from 5 to 8.5 and an electrical conductivity of 300 μS/cm or less, and the aqueous dispersion is subjected to thin film-forming treatment to obtain a thin film of the aqueous dispersion, followed by drying.

The present invention has been completed, based on these novel findings.

Accordingly, it is an object of the present invention to provide a novel excipient having not only high compactability but also an increased rate of disintegration.

It is another object of the present invention to provide a novel process for producing an excipient having not only high compactability but also an increased rate of disintegration.

The foregoing and other objects, features and advantages of the present invention will be apparent from the following detailed description and appended claims.

DETAILED DESCRIPTION OF THE INVENTION

In one aspect of the present invention, there is provided an excipient having high compactability, comprising white powdery microcrystalline cellulose obtained by subjecting a cellulose material to hydrolysis with acid or oxidative degradation with alkali, the microcrystalline cellulose having an average degree of polymerization of from 100 to 375, preferably from 190 to 210, and an acetic acid holding capacity of 280% or more, preferably from 290 to 370% and having a compression characteristic satisfying an equality of formula (1):

$$P \cdot \frac{V_o}{V_o - V_p} = \frac{1}{a \cdot b} + \frac{P}{a} \qquad (1)$$

wherein a is from 0.85 to 0.90, b is from 0.05 to 0.10, P represents the compression pressure (kgf/cm$^2$) applied to the microcrystalline cellulose, $V_o$ represents the apparent specific volume (cm$^3$/g) of the microcrystalline cellulose, and $V_p$ represents the specific volume (cm$^3$/g) of the microcrystalline cellulose at the compression pressure P.

The excipient of the present invention is substantially comprised of microcrystalline cellulose. The excipient of the present invention may contain components other than microcrystalline cellulose, such as hemicellulose, lignin and fats as long as the other components do not impair the effects of the present invention. The content of the other components is generally about 10% by weight or less.

The white powdery microcrystalline cellulose in the present invention is obtained from a cellulose material, such as purified wood pulp, bamboo pulp, cotton linter, ramie or the like by a method as mentioned below. The microcrystalline cellulose of the excipient of the present invention has an average degree of polymerization of from 100 to 375, preferably from 180 to 220, more preferably from 190 to 210. When the microcrystalline cellulose has an average degree of polymerization of less than 100, the compactability is lowered. On the other hand, when the microcrystalline cellulose has an average degree of polymerization of more than 375, it exhibits fibrous characteristics, so that the flowability is lowered. When the average degree of polymerization is in the preferred range from 180 to 220, an extremely improved balance can be achieved between the compactability and the rate of disintegration.

The microcrystalline cellulose of the excipient of the present invention has an acetic acid holding capacity of 280% or more, preferably from 290 to 370%, and has a compression characteristic satisfying Kawakita's equality of formula (1):

$$P \cdot \frac{V_o}{V_o - V_p} = \frac{1}{a \cdot b} + \frac{P}{a} \quad (1)$$

wherein a is from 0.85 to 0.90, b is from 0.05 to 0.10, P represents the compression pressure (kgf/cm$^2$) applied to the microcrystalline cellulose, $V_o$ represents the apparent specific volume (cm$^3$/g) of the microcrystalline cellulose, and $V_p$ represents the specific volume (cm$^3$/g) of the microcrystalline cellulose at the compression pressure P.

The terminology "acetic acid holding capacity" used herein means the amount of acetic acid which can be held by the pores of the powdery microcrystalline cellulose when the powdery microcrystalline cellulose is equilibrated with acetic acid. The acetic acid holding capacity can be determined by immersing a powdery microcrystalline cellulose, for 30 minutes, in acetic acid in an amount ten times by weight the weight of the powdery microcrystalline cellulose, subjecting the mixture of the microcrystalline cellulose and the acetic acid to centrifugation at 2,000 G to separate the mixture into a supernatant (acetic acid) and the microcrystalline cellulose, and measuring the amount of the acetic acid held in the pores of the microcrystalline cellulose. For measuring the amount of the acetic acid held in the pores of the microcrystalline cellulose, the weight ($W_1$) of the separated microcrystalline cellulose is measured, the microcrystalline cellulose is then dried, and the weight ($W_2$) of the dried microcrystalline cellulose is measured. The acetic acid holding capacity is calculated by the following formula:

$$\text{Acetic acid holding capacity} = \frac{W_1 - W_2}{W_2} \times 100\%$$

The acetic acid holding capacity is expressed in a weight percentage of the acetic acid which can be held by the microcrystalline cellulose, relative to the weight of the microcrystalline cellulose in a dry state.

Acetic acid, which can be absorbed by a powdery microcrystalline cellulose, does not have the activity to cause a dissociation of the hydrogen bonds which are formed between the free hydroxyl groups present in the amorphous region of a powdery microcrystalline cellulose, so that acetic acid does not cause a large swelling of the microcrystalline cellulose [R. Hasebe, K. Matsumoto, H. Maeda, Sen-i Gakkaishi, Vol. 12, pp. 203–207 (1955)] (the region containing the above-mentioned hydrogen bonds is generally called a "cornified" tissue region). Further, the centrifugation of the microcrystalline cellulose particles holding acetic acid conducted after the immersion in acetic acid serves to cause the microcrystalline cellulose particles to gather close to each other, thereby restricting the amount of acetic acid held between the cellulose particles to a minimum. Therefore, the acetic acid holding capacity obtained by the above method represents the porosity and strength of the microcrystalline cellulose particles. In the present invention, as mentioned above, the acetic acid holding capacity is required to be 280% or more. When the acetic acid holding capacity is less than 280%, compaction of the microcrystalline cellulose by compression becomes too high, so that the disintegration rate of a tablet containing the microcrystalline cellulose as an excipient is lowered.

Kawakita's equation [K. Kawakita and Y. Tsutsumi, Bull. Chem. Soc. Japan, Vol. 39, No. 7, pp. 1364–1368 (1966)] is an empirical formula representing a change in volume of a powder which is caused by compressing the powder. It is known that Kawakita's formula can apply well especially to a powder which undergoes a large change in volume in the initial stage of compaction. A powdery microcrystalline cellulose is one of the powders to which Kawakita's equation can apply well. In Kawakita's equation (1) shown above, a and b are parameters which are determined depending on the type of the powder. In the present invention, it is requisite that parameter a be in the range from 0.85 to 0.90, and parameter b be in the range from 0.05 to 0.10. When even one of a and b is smaller than the respective range, the compactability is lowered. On the other hand, when even one of a and b is higher than the respective range, compaction of the microcrystalline cellulose by compression becomes too high, so that the disintegration rate of a tablet containing the microcrystalline cellulose as an excipient is lowered.

The excipient of the present invention can be prepared by subjecting an aqueous dispersion of purified cellulose particles, which has a solids content of 40% or less and is substantially free of other substances, such as acid, alkali and decomposition by-products (such as saccharides, e.g. glucose and xylose) derived from a cellulose material, to heat treatment at 100° C. or more, followed by drying. Alternatively, the excipient of the present invention can also be prepared by another method in which the aqueous dispersion of purified cellulose particles is not necessarily subjected to the heat treatment. In this case, the solids content of the aqueous dispersion of purified cellulose particles is adjusted to 23% or less, and subjected to thin film-forming treatment to obtain a thin film of the aqueous dispersion, followed by drying.

Accordingly, in another aspect of the present invention, there is provided a process for preparing an excipient having high compactability, which comprises subjecting a cellulose material to hydrolysis with acid or oxidative degradation with alkali to form cellulose particles, subjecting the cellulose particles to purification to obtain aqueous purified cellulose particles, adjusting a water content of the aqueous purified cellulose particles to obtain an aqueous dispersion of the purified cellulose particles, wherein the aqueous dispersion has a solids content of 40% or less by weight, a pH value of from 5 to 8.5 and an electrical conductivity of 300 μS/cm or less, and subjecting the aqueous dispersion to heat treatment at 100° C. or more, followed by drying.

Hereinbelow, the process of the present invention for preparing an excipient having high compactability, which involves the heat treatment of the aqueous dispersion of purified cellulose particles, is described.

A cellulose material is subjected to hydrolysis with acid or oxidative degradation with alkali to obtain a reaction mixture containing cellulose particles. If desired, the cellulose material may be subjected to mechanical treatment, such as pulverization, before and/or after the hydrolysis or the oxidative degradation.

The hydrolysis with acid in the process of the present invention can be carried out by dipping, while stirring or agitating, the cellulose material in an aqueous solution of acid, such as hydrochloric acid, sulfuric acid, nitric acid, phosphoric acid or the like. It is preferred to use an aqueous solution of hydrochloric acid or sulfuric acid. The acid concentration of the solution is preferably 0.1 to 15%, more preferably 0.5 to 10% by weight. The oxidative degradation can be carried out by dipping, while stirring or agitating, the cellulose material in an aqueous solution of alkali, such as potassium hydroxide, sodium hydroxide, calcium hydroxide or barium hydroxide. It is preferred to use potassium hydroxide or sodium hydroxide. Alternatively, the oxidative degradation may be conducted by using an aqueous solution of an oxidizing agent, such as sodium hypochlorite, periodic acid or hydrogen peroxide, preferably sodium hypochlorite. With respect to the concentration of the alkali or oxidizing agent in the solution, the same range as that of the acid for the acid hydrolysis can be employed. Either of the hydrolysis and the oxidative degradation is preferably carried out at a temperature of from 60° to 140 ° C., more preferably from 90° to 130° C., for preferably from 10 to 180 minutes, more preferably from 20 to 120 minutes. The weight ratio of the cellulose material to be treated to the aqueous solution of the acid, alkali or oxidizing agent is preferably from 1:7 to 1:30, more preferably from 1:10 to 1:20. The hydrolysis or the oxidative degradation is carried out in an atmosphere of air or an inert gas under atmospheric pressure or super atmospheric pressure.

Since the thus obtained reaction mixture containing the cellulose particles also contains impurities (such as acid or alkali) as well as water, the impurities are removed by purification techniques, such as filtration, centrifugation and separation-purification by means of a dialysis membrane, to thereby obtain aqueous purified cellulose particles which generally have a solids content of 1 to 50% by weight.

In purification of the cellulose particles by methods other than the method in which separation-purification of the cellulose particles is performed by means of a dialysis membrane, the cellulose particles are collected from the reaction mixture and the collected cellulose particles are subsequently subjected to purification to obtain aqueous purified cellulose particles. In the separation-purification method using a dialysis membrane, the reaction mixture containing cellulose particles obtained by the hydrolysis or oxidative degradation of the cellulose material is directly subjected to treatment with a dialysis membrane to obtain aqueous purified cellulose particles.

The water content of the thus obtained aqueous purified cellulose particles is adjusted (reduced or increased depending on the water content of the obtained aqueous purified cellulose particles) to obtain an aqueous dispersion of the purified cellulose particles, which has a solids content of 40% or less by weight, a pH value of from 5 to 8.5, preferably a pH value of from 5.5 to 8.0, and an electrical conductivity of 300 µS/cm or less, preferably from 40 to 150 µS/cm.

When water is added to the aqueous purified cellulose particles for adjusting the water content of the aqueous purified cellulose particles to obtain an aqueous dispersion of the purified cellulose particles, the water to be added is preferably pure water. The water to be added may contain a water-soluble organic solvent (such as ethanol, acetone or isopropyl alcohol) in a small amount (about 20% or less, preferably about 10% or less).

It is preferred that the solids content of the aqueous dispersion of the purified cellulose particles be in the range from 5 to 23% by weight, since the use of this range of solids content of the aqueous dispersion particularly facilitates to increase not only the effects of the heat treatment but also the production efficiency of the powdery microcrystalline cellulose.

When the solids content of the aqueous dispersion of the purified cellulose particles is more than 23% to 40% by weight, the aqueous dispersion assumes a wet mass form, which does not exhibit flowability. This aqueous dispersion in wet mass form can also be used for the subsequent heat treatment and drying according to the process of the present invention.

The thus prepared aqueous dispersion is subjected to heat treatment at 100° C. or more, preferably 100° to 200° C., more preferably 110° to 130° C. followed by drying.

In the conventional processes for preparing a microcrystalline cellulose, also, a crude aqueous dispersion of cellulose particles experiences heating at 100° C. or more, for example, at the time of completion of the hydrolysis of a cellulose material with acid. However, large quantities of acid and various hydrolysis products are present in such a crude aqueous dispersion of non-purified cellulose particles, so that the aqueous dispersion does not actually experience heat treatment at 150° C. and, hence, does not undergo any structural changes described below. Therefore, the effects of the heat treatment at 100° C. or more in the process of the present invention are not achieved by the conventional processes.

With respect to the apparatus to be used for the heat treatment of an aqueous dispersion of purified cellulose particles in the process of the present invention, there is no particular limitation, and an ordinary autoclave, a heat exchanger for a high viscosity fluid (for example, Frytherm manufactured and sold by Shinko Pantec K. K., Japan) or the like can be used for conducting the heat treatment at 100° C. or more, preferably 100° to 200 ° C., more preferably 110° to 130° C. There is no particular limitation with respect to the time for the heat treatment as long as the aqueous dispersion of the purified cellulose particles reaches 100° C. or more. The temperature of the aqueous dispersion may be immediately lowered after reaching 100° C. or more and the aqueous dispersion may be kept at 100° C. or more for a period of, for example, 0.1 second or less, 1 second or less, 1 minute or less, 1 hour or less, several hours or less or many hours. However, since an aqueous dispersion of cellulose particles is extremely low in heat conductivity and thus it is rather difficult to quickly raise the temperature of the aqueous dispersion, especially when an ordinary autoclave is used for the heat treatment. Therefore, when an ordinary autoclave is employed, it is desired to conduct the heat treatment for a prolonged period of time so as to ensure that the entire aqueous dispersion reaches 100 ° C. or more. For example, when the aqueous dispersion has a volume of 1 liter and has a solids content of 18% and an ordinary autoclave is used for the heat treatment, a desirable time for the heat treatment is generally at least 1 hour. Alternatively, when the time for the heat treatment is not to be prolonged, it is desired to stir well the aqueous dispersion during the heat treatment. In this case, for example, when the aqueous dispersion has a volume of 1 liter and has a solids content of 18%, the time for the heat treatment is generally about 5 minutes or less, even when an ordinary autoclave is used for the heat treatment. When it is desired to confirm that the aqueous dispersion has reached 100° C. or more, the confirmation can be readily conducted by placing a commercially available temperature indicator (which indicates, by color change or the like, that a predetermined temperature has been reached) into the aqueous dispersion before subjected to the heat treatment. (Examples of commercially available temperature indicators include Thermo Labels Super Mini 3K-110, sold by Nichiyu Giken Kogyo K. K., Japan.)

When the aqueous dispersion is subjected to heat treatment at 100° C. or more, the purified cellulose particles interact with each other, and interact with hydrogen ions, hydroxide ions and water molecules (these ions and molecules also interact with each other). As a result of these various interactions, an increase in viscosity (gelation) of the heat-treated aqueous dispersion and a decrease in the pH value of the aqueous dispersion occur. With respect to the structure of such an aqueous dispersion gel obtained by the heat treatment, elucidation has not yet been made. However, it is presumed that the aqueous dispersion gel has a structure in which cellulose particles are associated with each other, and hydrogen ions, hydroxide ions and water molecules are also associated with each other and with the cellulose particles, to thereby form the gel. The structure of the gel is not destroyed even if the temperature thereof is lowered to room temperature. However, when the gel is stirred even gently by means of a glass rod or the like, the viscosity of the gel is quickly lowered, and simultaneously the pH value is increased, so that the viscosity and the pH value revert to the original values exhibited before the heat treatment. In this connection, however, it is to be noted that the essentially important effect of the heat treatment at 100 ° C. or more of an aqueous dispersion of purified cellulose particles is not such a macroscopic structural change to gel, but a microscopic structural change occurring with respect to the aqueous dispersion. This is because even if the macroscopic structure of the gel is destroyed, delicate aggregation of cellulose particles is still observed, indicating that the association of cellulose particles is still maintained on a microscopic level. Further evidence indicating that the association of cellulose particles is microscopically maintained can be found in the fact that a heat-treated aqueous dispersion exhibits high drying rate as compared to the non-heat-treated aqueous dispersion. The heat-treated aqueous dispersion exhibits a drying rate which is 10% or more higher than the drying rate of the non-heat-treated aqueous dispersion. The reason for the increased drying rate is believed to reside in that due to the association of the cellulose particles, the arrangement of the cellulose particles occurring in the course of drying becomes sparse, thereby facilitating the diffusion of water.

The heat treatment at 100° C. or more of the aqueous dispersion of purified cellulose particles is followed by drying, i.e., effecting evaporation of the water. Examples of drying methods includes conventional methods, such as a spray drying method in which a disk type or two-fluid nozzle type atomizer is employed for spraying the aqueous dispersion while blowing hot air, and a hot air drying method in which an oven dryer is employed. The "two-fluid nozzle" mentioned above is a nozzle having a double nozzle structure in which an inner nozzle for the aqueous dispersion is disposed at the center of an outer nozzle for air, and the aqueous dispersion spurting out of the inner nozzle meets the air spurting out of the outer nozzle at the outlets of the nozzles, thereby spraying the aqueous dispersion.

Herein, the term "followed by drying" means that the heat treatment is continued until the heat-treated dispersion is dried or the heat treatment is simply followed by drying of the heat-treated dispersion. The drying means a removal of water which is present either in liquid form or gaseous form. The drying may be conducted after completion of the heat treatment. The drying may be conducted after the heat-treated aqueous dispersion has been cooled down. The drying may be conducted simultaneously with the heat treatment.

Preferred examples of methods in which the heat treatment of the aqueous dispersion and the drying of the heat-treated aqueous dispersion are conducted simultaneously or continuously include a method in which a drum dryer or a belt dryer is used. There can also be mentioned a method in which a two-fluid nozzle is employed to spray the aqueous dispersion together with water steam which is at 100° C. or more. When a drum dryer is employed, it is preferred that aqueous dispersion of the purified cellulose particles have a solids content of from 10 to 23% by weight. Further, it is also preferred that the temperature of the surface of the drum be in the range from about 105° to about 150° C. Furthermore, it is preferred that the drum clearance (distance between a pair of drums), the rotation rate of each drum and the supply rate of the aqueous dispersion be appropriately selected so as to obtain a dried microcrystalline cellulose having a water content of from 3 to 5% by weight.

In a further aspect of the present invention, there is provided a process for preparing an excipient having high compactability, which comprises subjecting a cellulose material to hydrolysis with acid or oxidative degradation with alkali to form cellulose particles, subjecting the cellulose particles to purification to obtain aqueous purified cellulose particles, adjusting a water content of the aqueous purified cellulose particles to obtain an aqueous dispersion of the purified cellulose particles, wherein the aqueous dispersion has a solids content of 23% or less by weight, a pH value of from 5 to 8.5 and an electrical conductivity of 300 μS/cm or less, and subjecting the aqueous dispersion to thin film-forming treatment to obtain a thin film of the aqueous dispersion, followed by drying.

This alternative process of the present invention for preparing an excipient having high compactability, in which the heat treatment at 100° C. or more of an aqueous dispersion of purified cellulose particles, is not necessarily required, is explained below. In this process, it is requisite that the aqueous dispersion of the purified cellulose particles have a solids content of 23% or less by weight, a pH value of from 5 to 8.5 and an electrical conductivity of 300 μS/cm or less, and that the aqueous dispersion be subjected to thin film-forming treatment to obtain a thin film thereof, followed by drying. The thin film-forming treatment can be conducted by spreading the aqueous dispersion on a substrate, such as a glass plate, an aluminum plate or the like, to obtain a thin film of the aqueous dispersion. It is preferred that the aqueous dispersion to be subjected to thin film-forming treatment have a solids content of 15 to 20% by weight. The pH value and electrical conductivity of the aqueous dispersion are preferably from 5.5 to 8.0 and from 40 to 150 μS/cm, respectively.

After a thin film of the aqueous dispersion is obtained, the drying of the thin film can be conducted by a conventional method which does not involve heating. For example, the drying can be conducted by allowing the thin film to stand at room temperature or by blowing air to the thin film. Alternatively, the drying may be performed by means of a drum dryer or a belt dryer. It is preferred that the aqueous dispersion of the purified cellulose particles be subjected to heat treatment at 100° C. or more before subjecting the aqueous dispersion to thin film-forming treatment to obtain a thin film of the aqueous dispersion.

In the alternative process of the present invention, when it is desired to conduct a heat treatment at 100° C. or more of an aqueous dispersion of purified cellulose particles, there is no particular limitation with respect to the time when the heat treatment is conducted. For example, the heat treatment may be effected simultaneously with or after the thin film-forming treatment. In the case of the latter, the heat treatment may be conducted before or simultaneously with the drying. The temperature for the heat treatment is 100° C. or more, preferably 100° to 200° C., more preferably 110° to 130° C. Although the heat treatment is not necessarily required in the alternative process of the present invention, with respect to the general method for heat treatment, reference can be made to the method of the heat treatment described above in connection with the process of the present invention in which the heat treatment is required.

The reason has not yet been elucidated as to why a microcrystalline cellulose having high compactability and an increased rate of disintegration can be obtained by drying the aqueous dispersion in the form of a thin film. However, it is believed that when a thin film of the aqueous dispersion is formed and dried on the surface of the substrate (such as a glass plate), rod-shaped cellulose particles are caused to be formed and two-dimensionally arranged on the substrate, so that the shrinkage of the microcrystalline cellulose in the course of drying is restricted through the contact of the thin film with the substrate, to thereby suppress the cornification of microcrystalline cellulose.

As described in, for example, Examined Japanese Patent Application Publication Specification No. 40-26274, it has conventionally been known that a drum dryer can be used in the production of a microcrystalline cellulose. However, there is no prior art teaching or suggesting that all of the above-mentioned requirements for the process of the present invention are critical for obtaining a microcrystalline cellulose having high compactability and an increased rate of disintegration. In the conventional methods in which spray drying, hot air drying or the like is employed, even if air heated to 100° C. or more is blown, an aqueous dispersion of purified cellulose particles does not experience the heat treatment defined in the process of the present invention, because the drying of the aqueous dispersion is finished before the temperature of the aqueous dispersion reaches 100° C. due to the latent heat of vaporization of water. Further, it should be noted that in any of the conventional methods using spray drying or hot air drying, there is no teaching or suggesting techniques such that an aqueous dispersion is not subjected to thin film-forming treatment.

The powdery microcrystalline cellulose obtained by any of the processes of the present invention can be subjected to pulverizing and sieving to adjust the particle size distribution to a value suitable for use. With respect to the microcrystalline cellulose for the excipient of the present invention, when the particle size distribution is measured by a sieving method, it is preferred that substantially no residue is present after sifting with a sieve having openings of 355 μm, and that the average particle diameter expressed by the particle size corresponding to 50% by weight in cumulative distribution, be in the range from 30 to 120 μm. However, relatively large particles which are retained on a sieve having openings of 355 μm may be contained in the microcrystalline cellulose for the excipient of the present invention as long as the powder characteristics, such as flowability, are not lost. The amount of the relatively large particles is preferably 5% by weight or less. When the average particle diameter of the excipient is less than 30 μm, the quantity of particles having a small particle size is too large, so that the flowability of the excipient becomes poor and the rate of disintegration of a tablet containing the excipient is lowered. When the average particle diameter of the excipient exceeds 120 μm, the excipient becomes coarse, so that the compactability of the excipient and the mixability of the excipient with other powdery materials are lowered.

It is preferred that the microcrystalline cellulose for the excipient of the present invention have an apparent specific volume of from 4.0 to 6.0 cm$^3$/g and a tapping apparent specific volume of 2.4 cm$^3$/g or more. When the apparent specific volume of the excipient is less than 4.0 cm$^3$/g, the compactability is lowered. On the other hand, when the apparent specific volume of the excipient exceeds 6.0 cm$^3$/g, the flowability is lowered. When the tapping apparent specific volume of the excipient is less than 2.4 cm$^3$/g, a tablet containing the excipient is too densely compacted, so that the rate of disintegration of the tablet is lowered. The upper limit of the preferred range of the tapping apparent specific volume is the same as that (6.0 cm$^3$/g) of the apparent specific volume. It is more preferred that the microcrystalline cellulose in the present invention have an apparent specific volume of from 4.5 to 5.5 cm$^3$/g and a tapping apparent specific volume of from 2.5 to 3.1 cm$^3$/g or more.

It is preferred that the excipient of the present invention have a specific surface area of less than 20 m$^2$/g, as measured according to the BET nitrogen adsorption method. More preferably, the specific surface area is 1 to 10 m$^2$/g. The specific surface area is determined according to the isotherm equation of S. Brunauer, P. Emmett and E. Teller [see JACS, 60, 309 (1938)]. The BET nitrogen adsorption method is the most popular method for determining the specific surface area of a porous material. When the specific surface area is 20 m$^2$/g or more, the microcrystalline cellulose particles are necessarily caused to have pores having a pore diameter as large as about 0.01 μm or more, leading to a lowering of strengths of the particles, so that a tablet made from the microcrystalline cellulose particles is disadvantageously pressed too densely, thereby deteriorating the rate of disintegration.

As mentioned above, for the purpose of improving the compactability of microcrystalline cellulose, studies had been made so as to increase an apparent specific volume of the microcrystalline cellulose. However, nothing had been considered about a tapping apparent specific volume and a specific surface area and, hence, deterioration of the rate of disintegration has frequently occurred. The present inventors have unexpectedly found that when an aqueous dispersion of the purified cellulose particles which satisfies the specific conditions (as mentioned above) is provided and the aqueous dispersion is subjected to the subsequent specific treatment (as mentioned above) under the specific conditions (as mentioned above) for obtaining white powdery microcrystalline cellulose, each of the apparent specific volume, tapping apparent specific volume and specific surface area of the resultant microcrystalline cellulose can be controlled within respective specific ranges, and the obtained microcrystalline cellulose exhibits a good balance of a compactability and a rate of disintegration and can be used as an excellent excipient.

Explanation on the method for preparing a standard tablet, which is used for evaluation of various properties of compaction products produced using the excipient of the present invention, is now made. For preparing a standard tablet, a metallic mold device is used. The metallic mold device can be one which is similar to that used for preparing a potassium bromide tablet which is used in infrared absorption analysis. However, other types of metallic mold devices can also be used since when a standard tablet is formed by means of the mold device, evacuation of the mold device is not conducted. The mold device can be of a simple structure comprising a metallic die and a punch. The mold device can be of a type such that a compression force is applied to a powder on one side or both opposite sides thereof. For obtaining a cylindrical tablet, a punch having a circular flat surface (having an area of 1 cm$^2$) for compression is used. In such a mold is placed 500 mg (having water adsorbed thereon) of a microcrystalline cellulose powder. The powder is compressed at a pressure of 100 kgf/cm$^2$ for 10 seconds by means of a pressing apparatus (e.g., a hand press). The resultant compressed tablet is released from the mold to obtain a standard tablet. The pressing, pressure-maintaining and pressure-releasing operations for forming a compressed tablet can also be performed using a universal tension and compression tester (e.g., Autograph manufactured and sold by Shimadzu Corp., Japan).

The methods for measuring the breaking strength and the disintegration time of the standard tablet are now described. With respect to the measurement of the breaking strength, the circumference of the cylindrical standard tablet is held between a pair of flat plates arranged in parallel, and pressed by means of the flat plates. The breaking strength is defined as the value of the pressure at which the standard tablet is broken. The breaking strength-measuring apparatus is designed such that one of the pair of flat plates is fixed, and the other is movable at a constant rate. The moving rate is in the range from about 4 to about 13 cm/min. For measuring the breaking strength of the standard tablet, a commercially available tablet hardness measuring tester or the above-mentioned universal tension and compression tester can be used. The disintegration time of the tablet is measured according to "Testing method of disintegration" in the "Part B General Testing Methods" of "12th Revised Japanese Pharmacopoeia". That method is described hereinbelow under the heading "Disintegration time of tablet (sec):".

When the microcrystalline cellulose for the excipient of the present invention is fabricated into a cylindrical standard tablet by the method described above, it is preferred that the obtained standard tablet have a breaking strength of 10 kgf or more in a diametric direction thereof, and exhibit a disintegration time of 100 seconds or less.

As mentioned above, with respect to the tablets prepared from the conventional microcrystalline cellulose excipients, the higher the compactability, the longer the disintegration time. That is, excipients not only having high compactability but also exhibiting a short disintegration time have heretofore not been known. In general, from a practical viewpoint, it is required that a pharmaceutical tablet have a breaking strength of about 4 kgf or more in a diametric direction thereof (see "The Dosage Form of Pharmaceuticals" p. 157, published by Ishiyaku Publishers, Inc., Japan, 1983). With respect to a rapid dissolution type tablet (which is a pharmaceutical tablet for rapid release of an active ingredient, such that at least 75% of an active ingredient in the tablet is released and dissolved in the digestive liquid within 20 minutes after the tablet is orally taken), the disintegration time is required to be 15 minutes or less [see "Development of Pharmaceuticals", vol. 11 (entitled 'Unit Operations for Preparing Pharmaceutical Products and Machinery to Be Used for the Operations'), p. 65, published by Hirokawa Publishing Co., Japan, 1989]. However, when a conventional excipient is fabricated into a standard tablet by the above-mentioned method, the obtained standard tablet has a breaking strength as low as less than 10 kgf and/or exhibits a disintegration time as long as more than 100 seconds. Therefore, when such a conventional excipient is used for preparing a tablet of a type such that it is required to contain a large amount of a pharmaceutically active ingredient having poor compactability and is to be dissolved in a digestive liquid rapidly after orally taken (e.g., a drug tablet for cold), the obtained tablet cannot achieve required functions. That is, this tablet does not satisfy both of the above-mentioned two requirements, i.e., the breaking strength of about 4 kgf or more in a diametric direction thereof and the disintegration time of 15 minutes or less. By contrast, the excipient of the present invention can advantageously be used for preparing the above-mentioned type of tablet which is required to contain a large amount of a pharmaceutically active ingredient having poor compactability and is to be dissolved in a digestive liquid rapidly after orally taken, because it exhibits not only high compactability but also a short disintegration time of the tablet.

It is preferred that a standard tablet prepared from the microcrystalline cellulose for the excipient of the present invention have a breaking strength of 10 kgf or more in a diametric direction thereof while exhibiting a disintegration time of 100 seconds or less, preferably 90 seconds or less. It is especially preferred that the standard tablet have a breaking strength of 11 kgf or more while maintaining a disintegration time of 90 seconds or less. With the use of the excipient having such properties, excellent pharmaceutical tablets can be provided which are capable of avoiding abrasion or destruction during transportation and use thereof, while enjoying rapid release properties with respect to an active ingredient contained therein.

In the present invention, it is preferred that when the microcrystalline cellulose has a water content of from 5 to 6% by weight, the microcrystalline cellulose have a transverse relaxation time of 0.00024 second or less with respect to the water.

The transverse relaxation time can be determined as follows. When a solid sample having water adsorbed thereon is subjected to NMR spectroscopic analysis using a proton liquid NMR probe, one broad peak ascribed to the adsorbed water is obtained. The transverse relaxation time is calculated from the half value width of the peak.

The microcrystalline cellulose having a transverse relaxation time of more than 0.00024 second is not preferred because the compactability of the microcrystalline cellulose is lowered. The reason for this has not yet been elucidated. However, it is presumed as follows. The shorter transverse relaxation time means that the movement of water molecules of the adsorbed water is more restricted. This means that the number of hydroxyl groups on the cellulose molecule, which can be easily bonded to the molecules of the adsorbed water via hydrogen bond, is increased. One of the reasons for the excellent compression characteristic of microcrystalline cellulose has been known to reside in that when the microcrystalline cellulose particles are pressed to one another or pressed against other powdery materials under stress (e.g., a pharmaceutically active ingredient in powdery form), the hydroxyl groups present in the surface of the molecule of the microcrystalline cellulose, are caused to form hydrogen bonds via the molecules of the adsorbed water. Therefore, the shorter the transverse relaxation time, the larger the number of hydroxyl groups on the cellulose molecule, which serve to increase the number of hydrogen bonds formed between the hydroxyl groups on the microcrystalline cellulose and the molecules of the adsorbed water, which hydrogen bonds are effective for imparting high compactability to the microcrystalline cellulose. Conventionally, for improving the compactability of powdery materials, it has mainly been attempted to increase the packing density of the powdery materials, but the improvement of the compactability thereby is limited. By contrast, in the present invention, the compactability of the microcrystalline cellulose can be skillfully enhanced by adjusting a transverse relaxation time to 0.00024 second or less, so that the bonding strengths at points of contact between the microcrystalline cellulose particles and/or between the microcrystalline cellulose particles and other powdery materials are increased through the increase in number of hydrogen bonds formed therebetween.

The excipient of the present invention is used for preparing a pharmaceutical product in substantially the same manner as in the conventional excipients, but the following great advantages are to be noted.

The excipient of the present invention has high compactability as compared to any conventional binder, e.g., conventional microcrystalline cellulose. Therefore, when the excipient of the present invention is used as a binder for preparing tablets by direct compaction process of tableting, dry granulation process of tableting, wet granulation process of tableting and the like, it is possible to prepare desired tablets with the use of a relatively small quantity of the excipients and a relatively low compression pressure. Further, since the excipient of the present invention exhibits a short disintegration time, a desired pharmaceutical tablet having disintegration properties can be prepared using the excipient of the present invention without any disintegration agent or with a very small amount thereof, even if required. The excipient of the present invention can be advantageously used, particularly, for preparing a tablet of a type such that the quantity of an excipient is required to be limited, for example, a drug tablet for cold or a small tablet which contains a relatively large quantity of pharmaceutically active ingredient. The excipient of the present invention can also be advantageously used for preparing a granule-containing tablet which has to be prepared under relatively low compression force. Furthermore, the excipient of the present invention can be advantageously used for preventing powder from blocking and improving the fluidity of powder, and also for improving compactability of powder for capsules. Still further, the excipient of the present invention can be advantageously used as an agent for facilitating extrusion in the extrusion granulation, and as an agent for facilitating granulation in the wet granulation methods, e.g., fluidized bed granulation and high-speed agitating granulation.

The excipient of the present invention can also be used in various fields other than the pharmaceutical industry. For example, the excipient of the present invention can be used for preparing tablet-type confectionery, healthy foods, food fibers and an agent for improving tastes of foods in food industry, and a solid foundation in cosmetic industry. The excipient of the present invention can also be used as catalysts in ceramic industry.

PREFERRED EMBODIMENT OF THE INVENTION

The present invention will now be described in greater detail referring to the following Examples, Comparative Examples, Application Examples and Comparative Application Examples which should not be construed to be limiting the scope of the present invention.

Physical characteristics of powdery cellulose material, an aqueous dispersion of purified cellulose particles and a tablet prepared using microcrystalline cellulose as an excipient in Examples, Comparative Examples, Application Examples and Comparative Application Examples described below are measured according to the following methods.

pH value:

The temperature of an aqueous dispersion of purified cellulose particles is adjusted to 25° C. and then, the pH value of the resultant aqueous dispersion is measured by means of an apparatus for measuring a hydrogen ion concentration using a glass electrode (pH meter HM-20E, manufactured and sold by TOA Electronics Ltd., Japan).

Electrical conductivity ($\mu$S/cm):

The temperature of an aqueous dispersion of purified cellulose particles is adjusted to 25° C. and then, the electrical conductivity of the resultant aqueous dispersion is measured by means of an apparatus for measuring an electrical conductivity (SC51POCKET, manufactured and sold by Yokogawa Electric Corp., Japan).

Acetic acid holding capacity (%):

About 3 g of a powdery cellulose material is accurately weighed and then, the powdery cellulose material is dipped in acetic acid (purity: not less than 95%) having a weight 10-fold as much as that of the powdery cellulose material at room temperature for 30 minutes. The resultant mixture is subjected to centrifugation at 2,000 G for 10 minutes to thereby separate the mixture into a supernatant and a precipitate. The supernatant is removed to thereby obtain an wet mass of the powdery cellulose material wetted with acetic acid. The weight (W) of the obtained wet mass is measured and then, the wet mass is vacuum-dried with heating to thereby dry the powdery cellulose material. The weight ($W_o$) of the dried powdery cellulose material is measured, and the acetic acid holding capacity of the original powdery cellulose material is calculated according to the following formula:

$$\text{Acetic acid holding capacity (\%)} = 100 \cdot (W - W_o)/W_o$$

The above measurement and calculation are conducted twice to obtain two values with respect to acetic acid holding capacity, and an average of the two values is taken.

Compression characteristic [parameters a and b of formula (1)]:

0.50 g of a powdery cellulose material is placed in a single punch type metallic mold device to be used for forming a cylindrical tablet having a circular cross-sectional area of 1 cm². Then, the powdery cellulose material is compressed at 200 kgf/cm² for 10 seconds by hand press from one side of the metallic mold, to thereby form a cylindrical tablet having a circular cross-sectional area of 1 cm². Substantially the same procedure as mentioned above is repeated nine times. Thus, ten cylindrical tablets are obtained which have been compressed at 200 kgf/cm². Further, in substantially the same manner as mentioned above, four classes of tablets, each class consisting of ten cylindrical tablets, are prepared at compression pressures of 400, 800, 1,200 and 1,600 kgf/cm², respectively.

With respect to each class of the tablets, the weights and thicknesses of the ten tablets are measured, and the specific volumes of the ten tablets are obtained, so that 10 values of specific volumes are attained for each class, that is, 50 values for the five classes are obtained in total. Then, using the 50 specific volume values individually, the volume decrease ratio (C) of the powdery cellulose material is calculated from the following formula:

$$C = (V_o - V_p)/V_o$$

wherein $V_o$ represents the apparent specific volume (cm³/g) (described below) of the powdery cellulose material, and $V_p$ represents the specific volume (cm³/g) of the tablet.

Thus, 50 values of volume decrease ratios are obtained. With respect to the relationship between the compression pressure P and the value P/C, using the above 50 values, a regression line represented by the following formula:

$$P/C = S + P \cdot T$$

is obtained by the method of least squares. From the gradient T and the intercept S of the above formula, parameters a and b of formula (1) are calculated as follows.

$$a = 1/T$$

$$b = T/S$$

Particle size distribution and average particle diameter:

30 g of powdery cellulose material is sifted for 10 minutes for classification by means of a JIS standard sieve (Z8801-1987) attached to a Ro-Tap type sieving and shaking machine (Sieve Shaker, manufactured and sold by HEIKO SEISAKUSHO Ltd., Japan), and a particle size distribution (cumulative distribution) is determined. The particle size corresponding to 50 wt. % in cumulative distribution is taken as an average particle size. When the ratio of the sifting residue of particles having a particle size of 45 μm or less is relatively high, a particle size distribution (cumulative distribution) is determined by means of Air jet sieve (manufactured and sold by ALPINE, Germany), and the particle size corresponding to 50 wt. % in cumulative distribution is taken as an average particle size.

Apparent specific volume ($cm^3/g$):

An appropriate quantity of powdery cellulose material, which has a volume of from about 70 to about 100 $cm^3$, is provided The powdery cellulose material is lightly packed in a glass cylinder having a volume of 100 $cm^3$ over 2 to 3 minutes by means of a quantitative feeder. The upper surface portion of the packed powdery cellulose material is leveled by means of a soft brush and then, the volume of the packed powdery cellulose material is measured. The volume is divided by the weight of the packed powdery cellulose material.

Tapping apparent specific volume ($cm^3/g$):

After the measurement of the apparent specific volume as mentioned above, the glass cylinder containing the powdery cellulose material is subjected to tapping onto a stand made of a relatively soft material, for example, a rubber plate placed on a desk, from a height of several centimeters in an approximately vertical direction. The tapping is continued until the packing density of the powdery cellulose material is not increased by tapping any more. After completion of the tapping, the volume of the resultant powdery cellulose material is measured and divided by the weight thereof.

Average degree of polymerization:

A powdery cellulose material is dissolved in a cuprammonium solution, and the average degree of polymerization of the powdery cellulose material is determined by the solution viscosity method described in INDUSTRIAL AND ENGINEERING CHEMISTRY, Vol. 42., No. 3, p. 502–507 (1950).

Specific surface area ($m^2/g$):

The specific surface area is determined using nitrogen gas by means of FLOWSORB II 2300 (manufactured and sold by MICROMERITICS, U.S.A.) in accordance with the BET method.

Transverse relaxation time (sec):

The water content [=100×weight of water/(weight of water plus dry weight of the powdery cellulose material)] of the powdery cellulose material is adjusted to 5 to 6%, and the water content-adjusted powdery cellulose material is introduced into a tube for a liquid sample. The powdery cellulose material is subjected to NMR spectroscopic analysis by means of FT-NMR AC200P (manufactured and sold by BRUKER, Germany) using a proton liquid NMR probe, to thereby obtain one broad peak ascribed to the water. From the half value width of the obtained peak, the transverse relaxation time is calculated according to the following formula:

$$\text{transverse relaxation time (sec)} = \frac{1}{(\text{the half value width of the obtained peak} \times \pi)}$$

Weight of tablet (mg) and CV (coefficient of variation, %) of tablet weight:

The weight of each of ten tablets, which have been individually prepared under same compression conditions is measured to thereby obtain a standard deviation with respect to the ten tablets. This standard deviation is divided by the arithmetic average value of the weights of the ten tablets, to thereby obtain a CV value of tablet weight.

Breaking strength (kgf):

The circumference of each of ten tablets is held between a pair of flat plates arranged in parallel, and pressed by means of the flat plates. The breaking strength is defined as the value of the pressure at which the tablet is broken. In the following Examples, Comparative Examples, Application Examples and Comparative Application Examples, for measuring the breaking strength, TABLET TESTER model 6D (manufactured and sold by SCHLEUNIGER, Germany) was used. The measurement was conducted with respect to each of ten tablets prepared under same compression conditions, and an average value with respect to ten tablets is taken.

Disintegration time of tablet (sec):

The disintegration time is measured according to "The Testing Method for Disintegration" in the "Part B General Testing Methods" of "12th Revised Japanese Pharmacopoeia" published by Hirokawa Publishing Ltd., 1991, by means of a machine for testing disintegration (model NT-2HS, manufactured and sold by TOYAMA SANGYO Co., Ltd., Japan). That method is carried out as follows:

Apparatus

The apparatus for the disintegration test is comprised of a tester, a beaker having an inner diameter of approximately 110 mm and a height of approximately 155 mm, an appropriate heater, and a motor. Also, a supplementary disc or cylinder is used in accordance with the operating method described below.

Tester: The tester has upper and lower two plastic plates A, each having a diameter of 90 mm and a thickness of 6 mm. Each of the plates has six holes positioned along the circumference at regular intervals, and each of the holes has a diameter of 24 mm.

The lower surface of the lower plastic plate has, attached thereto, an acid resistant net B having a mesh size of 2.0 mm and a fiber diameter of 0.6 mm. Each of the upper surface of the upper plate and the lower surface of the lower plate has, attached thereto, an acid resistant metal plate C having a diameter of 90 mm and a thickness of 1 mm. With respect to the lower surface of the lower plate, the metal plate C is attached thereto through the net B mentioned above. The metal plate C has six holes each having a diameter of from 22 to 23 mm, and the six holes are positioned in register with the six holes on the respective plastic plate A. Six glass tubes D each having an inner diameter of 21.5±0.5 mm, an outer diameter of 23.5 mm, and a length of 77.5±2.5 mm, are fixed between the upper and lower plates, with both ends of the glass tubes respectively inserted into the holes on the upper and lower plates, with both ends of the glass tubes respectively inserted into the holes on the upper and lower plates, and the upper and lower plates are secured to each other by three bolts and three nuts. The lower end of a suspension rod G having a length of 80 mm is attached to the center of the upper plate, and the upper end of the suspension rod G is attached to a holder which is adapted to be able to be smoothly vertically, reciprocally moved by a motor. The structure of the tester may be modified, except that the requirements for the glass tube and net have to be satisfied.

Supplementary disc: The supplementary disc is a smooth, transparent cylindrical body made of plastic, having a height of 9.50±0.15 mm and a diameter of 20.70±0.15 mm, and having a specific gravity of from 1.18 to 1.20 g/cc. The disc has five holes, each having a diameter of 2 mm, which run through the disc from the upper surface to the lower surface. One of the holes is positioned at the center of the disc, and other four holes are positioned around the central hole along a circle at regular intervals, which circle has a radius of 6 mm and has its center at the center of disc.

The periphery of the disc has four V-shape grooves positioned at regular intervals. Each groove has a width of 9.5 mm at the top and a width of 1.6 mm at the bottom and has a depth of 2.55 mm at the top and a width of 1.6 mm at the bottom.

Operating method: Tablets

As a testing liquid, water is used. 6 sample tablets are, respectively, placed in the 6 glass tubes of the tester, and then, 6 supplementary discs are, respectively, placed in the 6 glass tubes so that the upper surface of each disc becomes upward. Subsequently, the tester is subjected to vertical, reciprocal movement for 30 minutes and then, the inside of the glass tubes are observed. When no residual matter is found, or when only a spongy-like, soft or muddy matter is found, the sample tablets are recognized to have passed the test.

When one of the 6 sample tablets remains in its original form or remains in the form of a broken piece, fresh six sample tablets are prepared, and the same test is repeated. When no residual matter is found, or when only a spongy-like, soft or muddy matter is found, the sample tablets are recognized to have passed the test. The testing is conducted with respect to each of six tablets prepared under same compression conditions, and an average value with respect to the six tablets is taken.

EXAMPLE 1

1 kg of commercially available dissolving pulp was finely divided, and hydrolyzed in 15 kg of a 10% aqueous solution of hydrochloric acid at 105° C. for 30 minutes to obtain a reaction mixture containing cellulose particles. The reaction mixture was subjected to filtration to collect the cellulose particles (acid-insoluble residue). The collected cellulose particles were subjected to washing, pH adjustment and concentration adjustment to thereby obtain an aqueous dispersion of purified cellulose particles. The aqueous dispersion of the purified cellulose particles had a solids content of 17% by weight, a pH value of 6.4 and an electrical conductivity of 120 μS/cm. The thus obtained aqueous dispersion of the purified cellulose particles was subjected to heat treatment and drying by means of a drum dryer (KDD-1, manufactured and sold by Kusuki Kikai Seisakusyo K. K., Japan), under conditions such that a steam pressure was 3.5 kgf/cm$^2$, a surface temperature of the drum was 136° C., a revolution rate of the drum was 2 rpm and a temperature of the aqueous dispersion in a liquid-storing portion of the drum dryer was 100° C., followed by pulverization by means of a hammer mill. The resultant powdery product was subjected to sifting by means of a sieve having openings of 425 μm to remove coarse particles, to thereby obtain excipient A. The properties of excipient A are shown in Table 1.

EXAMPLE 2

Substantially the same procedure as in Example 1 was conducted to obtain a reaction mixture containing cellulose particles, except that commercially available kraft pulp was used instead of commercially available dissolving pulp. The reaction mixture was subjected to filtration to collect the cellulose particles (acid-insoluble residue). The collected cellulose particles were subjected to washing, pH adjustment and concentration adjustment to thereby obtain an aqueous dispersion of purified cellulose particles. The aqueous dispersion of the purified cellulose particles had a solids content of 21%, a pH value of 8.4 and an electrical conductivity of 275 μS/cm. The thus obtained aqueous dispersion of the purified cellulose particles was subjected to heat treatment and drying by means of the drum dryer which was of the same type as used in Example 1, under conditions such that a steam pressure was 1.2 kgf/cm$^2$, a surface temperature of the drum was 110° C., a revolution rate of the drum was 0.5 rpm and a temperature of the aqueous dispersion in a liquid-storing portion of the drum dryer was 100° C., followed by pulverization by means of a hammer mill. The resultant powdery product was subjected to sifting by means of a sieve having openings of 425 μm to remove coarse particles, to thereby obtain excipient B. The properties of excipient B are shown in Table 1.

EXAMPLE 3

Substantially the same procedure as in Example 1 was conducted to obtain a reaction mixture containing cellulose particles. The reaction mixture was subjected to filtration to collect the cellulose particles (acid-insoluble residue). The collected cellulose particles were subjected to washing, pH adjustment and concentration adjustment to thereby obtain an aqueous dispersion of purified cellulose particles. The aqueous dispersion of the purified cellulose particles had a solids content of 18% by weight, a pH value of 7.2 and an electrical conductivity of 84 μS/cm. The thus obtained aqueous dispersion of the purified cellulose particles was subjected to heat treatment and drying by means of a spray dryer using two-fluid nozzle, in which the aqueous dispersion was sprayed with steam, under conditions such that a spray pressure was 4 kgf/cm$^2$ and a temperature of the steam was about 150° C. The resultant powdery product was subjected to sifting by means of a sieve having openings of 425 μm to remove coarse particles, to thereby obtain excipient C. The properties of excipient C are shown in Table 1.

Comparative Example 1

1 kg of commercially available dissolving pulp was finely divided, and hydrolyzed in 15 kg of a 10% aqueous solution of hydrochloric acid at 105° C. for 30 minutes to obtain a reaction mixture containing cellulose particles. The reaction mixture was subjected to filtration to collect the cellulose particles (acid-insoluble residue) and then, the collected cellulose particles were subjected to washing, to thereby obtain an aqueous dispersion of the cellulose particles. The aqueous dispersion of the cellulose particles had a solids content of 45% by weight, a pH value of 3.6 and an electrical conductivity of 40 μS/cm. The thus obtained aqueous dispersion of the cellulose particles was subjected to drying by means of an oven dryer at 80° C., followed by pulverization by means of a hammer mill. The resultant powdery product was subjected to sifting by means of a sieve having openings of 425 μm to remove coarse particles, to thereby obtain excipient D. The properties of excipient D are shown in Table 1.

Comparative Example 2

The excipient obtained in Comparative Example 1 was subjected to further pulverization by means of a jet mill (Single Track Jet Mill, manufactured and sold by Seishin Enterprise Co., Ltd., Japan) under conditions such that the air pressure was 7.0 kgf/cm$^2$ and the feeding rate of excipient D was 15 kg/hr, to obtain excipient E. Thereafter, substantially the same procedure as described above was conducted except that the feeding rate of the excipient D was changed to 2 kg/hr, to obtain excipient F. The thus obtained excipients E and F correspond to the excipient products obtained in Examined Japanese Patent Application Publication Specification No. 63–267731.

Comparative Example 3

1 kg of commercially available sulfite pulp was finely divided, and hydrolyzed in 20 kg of a 1% aqueous solution of sulfuric acid at 99° C. for 30 minutes to obtain a reaction mixture containing cellulose particles. The reaction mixture was subjected to filtration to collect the cellulose particles (acid-insoluble residue). The collected cellulose particles were subjected to washing, to thereby obtain an aqueous dispersion of the cellulose particles. The aqueous dispersion of the cellulose particles had a solids content of 49% by weight, a pH value of 3.8 and an electrical conductivity of 45 μS/cm. The thus obtained aqueous dispersion of the cellulose particles was subjected to drying by means of an oven dryer at 80° C., to thereby obtain dried cellulose particles having an average degree of polymerization of 452. The dried cellulose particles were subjected to pulverization by means of a hammer mill, followed by further pulverization by means of a ceramic ball mill for 12 hours. The resultant powdery product was subjected to sifting by means of a sieve having openings of 452 μm to remove coarse particles, to thereby obtain excipient G. Excipient G corresponds to the excipient product obtained in Examined Japanese Patent Application Publication Specification No. 51-17172. The properties of excipient G are shown in Table 1.

With respect to each of excipients A to C (Examples 1 to 3, respectively) and excipients D to G (Comparative Examples 1 to 3), the respective specific volume values of ten tablets, which are to be used for obtaining parameters a and b of Kawakita's formula, are shown in Tables 7(A)–7(G).

Application Examples 1 to 3

The above-obtained excipients A, B and C were individually fabricated into tablets in Application Examples 1, 2 and 3, respectively.

150 g of the above-obtained excipient (with respect to A, B and C, individually), and 600 g of lactose (Pharmatose 100M, manufactured and sold by De Melkindustrie Veghel by, the Netherlands) were placed in a polyethylene bag and mixed well by shaking for 3 minutes to thereby obtain a mixture. To the obtained mixture was added 3.75 g of magnesium stearate and further mixed by shaking for 30 seconds. The resultant mixture was fabricated into tablets by means of a rotary type tableting machine (CLEANPRESS CORRECT 12HUK, manufactured and sold by Kikusui Seisakusyo K. K., Japan) provided with a turn table having 12 dies and with 12 punches, in which each punch had a concave of 12R at a punching surface thereof and had a diameter of 8 mm and the revolution rate of a turn table was 25 rpm, to thereby obtain tablets each having a weight of 200 mg. The properties of each of the obtained tablets are shown in Table 2.

Comparative Application Examples 1 to 3

Substantially the same procedure as in Application Example 1 was conducted except that excipients D, E and G were used, to thereby obtain tablets each having a weight of 200 mg (Comparative Application Examples 1, 2 and 3, respectively). The properties of the obtained tablets are shown in Table 2.

As is apparent from Table 2, when excipient E is fabricated into a tablet (Comparative Application Example 2), the breaking strength becomes high in accordance with the increase of compression force, but the disintegration time is prolonged. When excipient D or excipient G is fabricated into a tablet (Comparative Application Example 1 or 3, respectively), the disintegration time is not prolonged even if the compression force is increased, but the breaking strength does not increase sufficiently.

By contrast, when the tablets are prepared using the excipient of the present invention (Application Examples 1 to 3), the breaking strength increases markedly in accordance with the increase of the compression force, while enjoying rapid disintegration. Particularly, with respect to excipients A and C (Application Examples 1 and 3, respectively) (the respective standard tablets produced therefrom exhibit the breaking strength of 11 kgf or more), the respective tablets prepared using the excipients also have an excellent breaking strength and exhibit a short disintegration time in good balance. That is, according to the present invention, a tablet, which not only has high breaking strength, but also exhibits a short disintegration time, is obtained.

EXAMPLE 4

1 kg of commercially available dissolving pulp was finely divided, and hydrolyzed in 18 kg of a 4% aqueous solution of sulfuric acid at 105° C. for 3 hours to obtain a reaction mixture containing cellulose particles. The reaction mixture was subjected to filtration to collect the cellulose particles (acid-insoluble residue). The collected cellulose particles were subjected to washing, pH adjustment and concentration adjustment to thereby obtain an aqueous dispersion of purified cellulose particles. The aqueous dispersion of the purified cellulose particles had a solids content of 17% by weight, a pH value of 6.0 and an electrical conductivity of 62 μS/cm. The thus obtained aqueous dispersion of the purified cellulose particles was dried in the same manner as in Example 1, followed by pulverization by means of a hammer mill. The resultant powdery product was subjected to sifting by means of a sieve having openings of 425 μm to remove coarse particles, to thereby obtain excipient H. The properties of excipient H are shown in Table 3.

EXAMPLE 5

Substantially the same procedure as in Example 1 was conducted to obtain a reaction mixture containing cellulose particles. The reaction mixture was subjected to filtration to collect the cellulose particles (acid-insoluble residue). The collected cellulose particles were subjected to washing, pH adjustment and concentration adjustment to thereby obtain an aqueous dispersion of purified cellulose particles. The aqueous dispersion of the purified cellulose particles had a solids content of 18% by weight, a pH value of 7.3 and an electrical conductivity of 113 µS/cm. The thus obtained aqueous dispersion of the purified cellulose particles was placed in an autoclave and then, the aqueous dispersion was heated at 121° C. for 2 hours. Thereafter, the aqueous dispersion was allowed to stand still and cooled. When the aqueous dispersion was taken out of the autoclave, the temperature thereof was 95° C. Then, the aqueous dispersion was coated on a glass plate, so that the aqueous dispersion formed a thin film having a thickness of 1 mm on the glass plate. The thin film was dried by means of an oven dryer at 80° C. The dried thin film was peeled off from the glass plate and subjected to pulverization by a hammer mill. The resultant powdery product was subjected to sifting by means of a sieve having openings of 425 µm to remove coarse particles, to thereby obtain excipient I. The properties of excipient I are shown in Table 3.

Comparative Example 4

Substantially the same procedure as in Example 1 was conducted except that dissolving pulp was hydrolyzed for only 5 minutes, to thereby obtain an aqueous dispersion of the cellulose particles. The aqueous dispersion of the cellulose particles had a solids content of 17% by weight, a pH value of 8.1 and an electrical conductivity of 38 µS/cm. The thus obtained aqueous dispersion of the cellulose particles were dried in the same manner as in Example 1. Then, the dried cellulose particles were pulverized by a flush mill (FL-200, manufactured by Fuji Paudal Co., Ltd., Japan) and subjected to sifting by means of a sieve having openings of 425 µm to remove coarse particles, to thereby obtain excipient J. The properties of excipient J are shown in Table 3.

Comparative Example 5

1 kg of rayon yarn waste was finely divided, and was hydrolyzed in 30 kg of a 0.3% aqueous solution of hydrochloric acid at 100° C. for 40 minutes to obtain a reaction mixture containing cellulose particles. The reaction mixture was subjected to decantation to wash the cellulose particles (acid-insoluble residue). The resultant cellulose particles were subjected to filtration, pH adjustment and concentration adjustment to thereby obtain an aqueous dispersion of purified cellulose particles. The aqueous dispersion of the purified cellulose particles had a solids content of 10% by weight, a pH value of 7.3 and an electrical conductivity of 310 µS/cm. The thus obtained aqueous dispersion of purified cellulose particles was dried in the same manner as in Example 1, followed by pulverization by the jet mill which was of the same type as used in Comparative Example 2. The resultant powdery product was subjected to sifting by means of a sieve having openings of 425 µm to remove coarse particles, to thereby obtain excipient K. The properties of excipient K are shown in Table 3.

Comparative Example 6

Substantially the same procedure as in Comparative Example 1 was conducted to obtain a reaction mixture containing cellulose particles. The reaction mixture was subjected to filtration to collect the cellulose particles (acid-insoluble residue). The collected cellulose particles were subjected to washing and dehydration to thereby obtain a wet mass of purified cellulose particles having a water content of 50% by weight, a pH value of 3.5 and an electrical conductivity of 41 µS/cm. The wet mass was dispersed in the isopropyl alcohol, and the resultant mixture was twice subjected to filtration, liquid removal and redispersion. Then, the purified cellulose particles were subjected to treatment for dispersion three times by means of a homogenizer (Gaulin Homogenizer model 15M, manufactured by Nippon Seiki Seisakusyo K.K., Japan) at a compression pressure of 400 kgf/cm$^2$ to obtain a slurry containing the purified cellulose particles. To the thus obtained slurry was further added isopropyl alcohol so that the resultant isopropyl alcohol slurry containing the purified cellulose particles had a solids content of 10% by weight. The isopropyl alcohol slurry was spray-dried by means of a nitrogen-circulation type spray dryer, under conditions such that the temperature of the introduced air was 150° C. and that of the expelled air was 83° C. so that the heat treatment and drying of the isopropyl alcohol slurry containing the purified cellulose particles were finished at a temperature of 83° C. The resultant powdery product was subjected to sifting by means of a sieve having openings of 425 µm to remove coarse particles, to thereby obtain excipient L which corresponds to the excipient product obtained in Unexamined Japanese Patent Application Laid-Open Specification No. 2-84401. With respect to excipient L, the total pore volume of the pores having pore diameters of 0.01 µm or more was 0.7 cm$^3$/g as measured by means of a mercury porosimeter. The properties of excipient L are shown in Table 3.

Comparative Example 7

1 kg of commercially available dissolving pulp was finely divided, and hydrolyzed in 20 kg of a 0.5% aqueous solution of hydrochloric acid at 121° C. for 1 hour to obtain a reaction mixture containing cellulose particles. The reaction mixture was subjected to filtration to collect the cellulose particles (acid-insoluble residue). The collected cellulose particles were subjected to washing and dehydration to thereby obtain an aqueous dispersion of purified cellulose particles. The aqueous dispersion of the cellulose particles had a solids content of 48%, a pH value of 3.4 and an electrical conductivity of 53 µS/cm. The thus obtained aqueous dispersion was subjected to drying by means of a vacuum dryer at 70° C. to thereby obtain a dried cellulose particles having a water content of 4.2% by weight. The dried cellulose particles were subjected to pulverization by means of a hammer mill. The resultant powdery product was subjected to sifting by means of a sieve having openings of 425 µm to remove coarse particles, to thereby obtain excipient M. Excipient M corresponds to the excipient product obtained in Examined Japanese Patent Application Publication Specification No. 40-26274. The properties of excipient M are shown in Table 1.

With respect to each of excipients H and I (Examples 4 and 5, respectively) and excipients J to M (Comparative Examples 4 to 7, respectively), the respective specific volume values of ten tablets, which are to be used for obtaining parameters a and b of Kawakita's formula, are shown in Tables 7(H) to 7(M).

Application Examples 4 and 5

The above-obtained excipients H and I were individually fabricated into tablets in Application Examples 4 and 5, respectively.

In Application Examples 4 and 5, substantially the same procedure as in Application Example 1 was individually conducted except that 70 g of excipient (with respect to H and I, individually), 630 g of lactose (Pharmatose 100M, manufactured and sold by De Melkindustrie Veghel bv, the Netherlands) and 3.5 g of magnesium stearate (manufactured and sold by Taihei Kagaku Sangyou K. K., Japan) were used, to obtain respective tablets. The properties of the obtained tablets are shown in Table 4.

Comparative Application Examples 4 to 7

Substantially the same procedure as in Application Example 4 was conducted except that excipients J, K, L and M were individually used instead of excipient H, to obtain respective tablets (Comparative Application Examples 4, 5, 6 and 7, respectively). The properties of the obtained tablets are shown in Table 4.

As is apparent from Table 4, when excipient L is fabricated into a tablet (Comparative Application Example 6), the breaking strength becomes high in accordance with the increase of the compression force, but the disintegration time is prolonged. When excipient J is fabricated into a tablet (Comparative Application Example 4), the breaking strength is not increased sufficiently even if the compression force is increased, and the disintegration time is prolonged. Further, the cellulose particles of excipient J have an average particle diameter of more than 120 μm, so that the excipient exhibits low fluidity. Accordingly, the CV of tablet weight is increased. When excipient K or M was fabricated into a tablet (Comparative Application Example 5 or 7, respectively), extremely rapid disintegration is observed despite the increase of the compression force, but the breaking strength is not increased sufficiently.

By contrast, when excipient H (Application Example 4) and excipient I (Application Example 5) of the present invention is fabricated into tablets, although the content of each of excipients H and I in respective tablets is as low as about 10% by weight, the breaking strength of each of the tablets becomes remarkably high in accordance with the increase of compression force, while enjoying rapid disintegration. Further, the excipients H and I have low CV of tablet weight. That is, when any of the excipients H and I is used for preparing a tablet, a tablet having not only a high breaking strength and a high uniformity in weight but also exhibiting a short disintegration time can be produced even at a relatively low content of the excipient.

EXAMPLE 6

Substantially the same procedure as in Example 1 was conducted to obtain a reaction mixture containing cellulose particles. The reaction mixture was subjected to filtration to collect the cellulose particles (acid-insoluble residue). The collected cellulose particles were subjected to washing, pH adjustment and concentration adjustment to thereby obtain an aqueous dispersion of purified cellulose particles. The aqueous dispersion of the purified cellulose particles had a solids content of 19% by weight, a pH value of 6.6 and an electrical conductivity of 125 μS/cm. The thus obtained aqueous dispersion of the purified cellulose particles was subjected to heat treatment and drying by means of the drum dryer which was of the same type as used in Example 1, under conditions such that a steam pressure was 5 kgf/cm$^2$, a surface temperature of the drum was 143° C., a revolution rate of the drum was 5 rpm and a temperature of the aqueous dispersion in a liquid-storing portion of the drum dryer was 100° C., followed by pulverization by means of a flush mill (model FL-200, manufactured and sold by Fuji Paudal Co., Ltd., Japan). The resultant powdery product was subjected to sifting by means of a sieve having openings of 425 μm to remove coarse particles, to thereby obtain excipient N. The properties of excipient N are shown in Table 5.

EXAMPLE 7

1 kg of refined linters was sufficiently disentangled. With respect to the subsequent procedure for obtaining a reaction mixture containing cellulose particles, substantially the same procedure as in Example 1 was conducted. The resultant reaction mixture was subjected to filtration to collect the cellulose particles (acid-insoluble residue). The collected cellulose particles were subjected to washing, pH adjustment and concentration adjustment to thereby obtain an aqueous dispersion of purified cellulose particles. The aqueous dispersion of the purified cellulose particles had a solids content of 20% by weight, a pH value of 8.2 and an electrical conductivity of 54 μS/cm. The thus obtained aqueous dispersion of the purified cellulose particles was subjected to heat treatment and drying by means of the drum dryer which was of the same type as used in Example 1, under conditions such that a steam pressure was 3 kgf/cm$^2$, a surface temperature of the drum was 131° C., a revolution rate of the drum was 1 rpm and a temperature of the aqueous dispersion in a liquid-storing portion of the drum dryer was 100° C., followed by pulverization by means of a hammer mill. The resultant powdery product was subjected to sifting by means of a sieve having openings of 425 μm to remove coarse particles, to thereby obtain excipient O. The properties of excipient O are shown in Table 5.

Comparative Example 8

Substantially the same procedure as in Example 1 was conducted except that hydrolysis was conducted for only 5 minutes to thereby obtain excipient P. In the above procedure, the aqueous dispersion containing purified cellulose particles (which was subjected to heat treatment and drying to obtain excipient P) had a solids content of 17% by weight, a pH value of 6.5 and an electrical conductivity of 100 μS/cm. The properties of excipient P are shown in Table 5.

Comparative Example 9

A commercially available microcrystalline cellulose, Avicel® PH-101 (manufactured and sold by Asahi Kasei Kogyo Co., Ltd., Japan) was used as excipient Q. The properties of excipient Q are shown in Table 5.

Comparative Example 10

A commercially available microcrystalline cellulose, Avicel® PH-301 (manufactured and sold by Asahi Kasei Kogyo Co., Ltd., Japan) was used as excipient R. Excipient R has a repose angle of 41° and corresponds to the excipient product obtained in Japanese Patent Application Publication Specification No. 56-38128. The properties of excipient R are shown in Table 5.

Comparative Example 11

A commercially available microcrystalline cellulose, GRADE M-101 (manufactured and sold by Ming Tai Chemical Co., Ltd., Taiwan) was used as excipient S. The properties of excipient S are shown in Table 5.

With respect to each of excipients N and O (Examples 6 and 7, respectively) and excipients P to S (Comparative Examples 8 to 11, respectively), the respective specific volume values of ten tablets, which are to be used for obtaining parameters a and b of Kawakita's formula, are shown in Tables 7(N) to 7(S).

Application Examples 6 and 7

The above-obtained excipients N and O were individually fabricated into tablets in Application Examples 6 and 7, respectively.

150 g of the above-obtained excipient (with respect to N and O, individually), 150 g of phenacetin (manufactured and sold by Yamamoto Kagaku Kogyo K. K., Japan) and 450 g of lactose (Pharmatose 100M, manufactured and sold by De Melkindustrie Veghel bv, the Netherlands) were placed in a polyethylene bag and mixed well by shaking for 3 minutes. To the obtained mixtures was added 3.75 g of magnesium stearate (manufactured and sold by Taihei Kagaku Sangyou K. K., Japan) and further mixed by shaking for 30 seconds. The resultant mixtures was fabricated into tablets each having a weight of 200 mg by means of the same rotary type tableting machine (CLEANPRESS CORRECT 12 HUK, manufactured and sold by Kikusui Seisakusyo K.K., Japan) as used in Application Examples 1 to 3, in which each punch had a concave of 12R at a punching surface thereof and had a diameter of 8 mm and the revolution rate of a turn table was 25 rpm, to thereby obtain tablets each having a weight of 200 mg. The properties of each of the obtained tablets are shown in Table 6.

Comparative Application Examples 8 to 12

Substantially the same procedure as in Application Example 6 was conducted except that excipents F, P, Q, R and S were used instead of excipient N, to thereby obtain tablets each having a weight of 200 mg (Comparative Application Examples 8 to 12, respectively). The properties of the obtained tablets are shown in Table 6.

As is apparent from Table 6, when excipient F is fabricated into a tablet (Comparative Application Example 8), the breaking strength becomes high in accordance with the increase of compression force, but the disintegration time is prolonged. Further, excipient F has a small average particle diameter and a large apparent specific volume, so that the excipient exhibits low fluidity. Accordingly, the tablet prepared using excipient has a high CV of tablet weight. When excipient P is fabricated into a tablet (Comparative Application Example 9), the disintegration rate is markedly lowered despite the increase of the compression force, but the breaking strength is not increased sufficiently. Similar results are obtained in Comparative Application Examples 10, 11 and 12.

By contrast, when the tablets are prepared using the excipient of the present invention (Application Examples 6 and 7), the breaking strength is increased markedly in accordance with the increase of the compression force, while enjoying rapid disintegration and low CV of tablet weight. That is, according to the present invention, a tablet, which has not only high breaking strength and high uniformity in weight, but also exhibits a short disintegration time, is obtained.

TABLE 1

| | | | | | | | | | | | | | |
|---|---|---|---|---|---|---|---|---|---|---|---|---|---|
| | | | | Powdery microcrystalline cellulose | | | | | | | | | |
| | | | Acetic acid holding capacity [%] | Kawakita's formula | | Average particle diameter [μm] | >355 μm [wt %] | Apparent specific volume [cm³/g] | Tapping apparent specific volume [cm³/g] | Specific surface area [m²/g] | Transverse relaxation time [s] | Standard tablet | |
| | Excipient | Average degree of polymerization | | a | b | | | | | | | Breaking strength [kgf] | Disintegration time [sec] |
| Example Nos. | | | | | | | | | | | | | |
| 1 | A | 205 | 330 | 0.892 | 0.0860 | 47 | 1 | 5.4 | 2.7 | 1.9 | 0.000200 | 14.2 | 55 |
| 2 | B | 163 | 305 | 0.852 | 0.0510 | 38 | 0 | 4.6 | 2.7 | 1.6 | 0.000237 | 10.5 | 43 |
| 3 | C | 196 | 285 | 0.872 | 0.0621 | 42 | 0 | 5.5 | 3.0 | 1.5 | 0.000217 | 11.3 | 41 |
| Comparative Example Nos. | | | | | | | | | | | | | |
| 1 | D | 202 | 271 | 0.841 | 0.0485 | 45 | 1 | 3.0 | 2.1 | 1.1 | 0.000247 | 9.3 | 10 |
| 2 | E | 202 | 241 | 0.845 | 0.0543 | 25 | 0 | 4.3 | 2.3 | 1.5 | 0.000252 | 11.5 | 410 |
| | F | 202 | 272 | 0.912 | 0.1080 | 8 | 0 | 6.4 | 2.3 | 4.2 | 0.000243 | 15.8 | 930 |
| 3 | G | 405 | 263 | 0.774 | 0.0333 | 55 | 3 | 3.1 | 2.5 | 0.6 | 0.000281 | 6.7 | 42 |

TABLE 2

| Application Example Nos. | Excipient | Compression force [kgf] | Breaking strength [kgf] | Disintegration time [sec] |
|---|---|---|---|---|
| 1 | A | 500 | 4.1 | 13 |
|  |  | 1000 | 8.4 | 27 |
|  |  | 1500 | 11.3 | 55 |
|  |  | 2000 | 13.1 | 68 |
| 2 | B | 500 | 3.2 | 10 |
|  |  | 1000 | 7.2 | 25 |
|  |  | 1500 | 10.2 | 46 |
|  |  | 2000 | 11.9 | 60 |
| 3 | C | 500 | 4.0 | 6 |
|  |  | 1000 | 8.0 | 22 |
|  |  | 1500 | 10.8 | 40 |
|  |  | 2000 | 12.5 | 51 |
| Comparative Application Example Nos. |  |  |  |  |
| 1 | D | 500 | 2.5 | 3 |
|  |  | 1000 | 5.5 | 8 |
|  |  | 1500 | 7.1 | 17 |
|  |  | 2000 | 9.0 | 21 |
| 2 | E | 500 | 4.1 | 25 |
|  |  | 1000 | 7.8 | 62 |
|  |  | 1500 | 10.1 | 107 |
|  |  | 2000 | 11.4 | 144 |
| 3 | G | 500 | 1.8 | 8 |
|  |  | 1000 | 4.0 | 17 |
|  |  | 1500 | 5.5 | 23 |
|  |  | 2000 | 6.8 | 32 |

TABLE 3

| | | Powdery microcrystalline cellulose | | | | | | | | | Standard tablet | |
|---|---|---|---|---|---|---|---|---|---|---|---|---|
| | | Average degree of polymerization | Acetic acid holding capacit [%] | Kawakita's formula a | Kawakita's formula b | Average particle diameter [µm] | >355 µm [wt %] | Apparent specific volume [cm³/g] | Tapping apparent specific volume [cm³/g] | Specific surface area [m²/g] | Breaking strength [kgf] | Disintegration time [sec] |
| | Excipient | | | | | | | | | | | |
| Example Nos. | | | | | | | | | | | | |
| 4 | H | 209 | 353 | 0.876 | 0.0736 | 32 | 0 | 5.9 | 3.1 | 1.6 | 12.9 | 76 |
| 5 | I | 205 | 322 | 0.865 | 0.0585 | 31 | 0 | 5.2 | 2.6 | 1.3 | 11.1 | 50 |
| Comparative Example Nos. | | | | | | | | | | | | |
| 4 | J | 380 | 374 | 0.758 | 0.0240 | 125 | 5 | 4.9 | 3.0 | 0.6 | 5.9 | 98 |
| 5 | K | 72 | 193 | 0.727 | 0.0236 | 28 | 0 | 2.3 | 2.0 | 0.7 | 4.6 | 2 |
| 6 | L | 197 | 271 | 0.899 | 0.0132 | 44 | 2 | 5.9 | 2.9 | 30.0 | 16.0 | 125 |
| 7 | M | 216 | 248 | 0.793 | 0.0349 | 32 | 0 | 2.9 | 2.1 | 1.2 | 6.9 | 7 |

TABLE 4

| | Excipient | Compression force [kgf] | Tablet weight [mg] | CV of tablet weight [%] | Breaking strength [kgf] | Disintegration time [sec] |
|---|---|---|---|---|---|---|
| Application Example Nos. | | | | | | |
| 4 | H | 500 | 200.0 | 0.3 | 2.1 | 5 |
| | | 1000 | 200.4 | 0.6 | 5.0 | 14 |
| | | 1500 | 201.5 | 0.6 | 6.7 | 25 |
| | | 2000 | 201.3 | 0.3 | 8.7 | 36 |
| 5 | I | 500 | 200.1 | 0.8 | 2.8 | 6 |
| | | 1000 | 199.6 | 0.7 | 4.7 | 11 |
| | | 1500 | 199.9 | 0.8 | 6.2 | 17 |
| | | 2000 | 200.2 | 0.5 | 7.8 | 26 |
| Comparative Application Example Nos. | | | | | | |
| 4 | J | 500 | 199.5 | 1.5 | 1.5 | 8 |
| | | 1000 | 199.6 | 1.3 | 3.2 | 16 |
| | | 1500 | 200.3 | 1.5 | 4.3 | 24 |
| | | 2000 | 201.2 | 1.7 | 4.9 | 28 |
| 5 | K | 500 | 199.3 | 0.6 | 1.2 | 2 |
| | | 1000 | 200.6 | 0.8 | 2.4 | 4 |
| | | 1500 | 200.4 | 0.6 | 3.2 | 6 |
| | | 2000 | 200.2 | 0.4 | 4.0 | 6 |
| 6 | L | 500 | 201.1 | 0.5 | 3.2 | 22 |
| | | 1000 | 200.8 | 0.6 | 5.9 | 41 |
| | | 1500 | 200.8 | 0.6 | 8.0 | 61 |
| | | 2000 | 200.5 | 0.3 | 9.5 | 89 |
| 7 | M | 500 | 199.1 | 1.1 | 1.5 | 4 |
| | | 1000 | 199.6 | 0.9 | 3.5 | 7 |
| | | 1500 | 200.1 | 0.9 | 4.6 | 10 |
| | | 2000 | 199.7 | 0.7 | 5.6 | 11 |

TABLE 5

| | | Powdery microcrystalline cellulose | | | | | | | | | Standard tablet | |
|---|---|---|---|---|---|---|---|---|---|---|---|---|
| | | Average degree of polymer-ization | Acetic acid holding capac-ity [%] | Kawakita's formula a | Kawakita's formula b | Average particle diameter [μm] | >355 μm [wt %] | Apparent specific volume [cm³/g] | Tapping apparent specific volume [cm³/g] | Specific surface area [m²/g] | Breaking strength [kgf] | Disinte-gration time [sec] |
| | Excipient | | | | | | | | | | | |
| Example Nos. | | | | | | | | | | | | |
| 6 | N | 194 | 284 | 0.873 | 0.0547 | 118 | 4 | 4.8 | 2.6 | 1.2 | 13.1 | 95 |
| 7 | O | 220 | 282 | 0.853 | 0.0503 | 39 | 0 | 4.1 | 2.4 | 1.7 | 10.2 | 25 |
| Comparative Example Nos. | | | | | | | | | | | | |
| 8 | P | 380 | 401 | 0.776 | 0.0282 | 82 | 3 | 5.5 | 3.2 | 0.8 | 6.1 | 23 |
| 9 | Q | 214 | 264 | 0.797 | 0.0329 | 47 | 0 | 3.2 | 2.2 | 1.1 | 7.0 | 6 |
| 10 | R | 160 | 181 | 0.730 | 0.0211 | 48 | 2 | 2.4 | 1.7 | 0.6 | 5.5 | 3 |
| 11 | S | 190 | 252 | 0.791 | 0.0302 | 45 | 0 | 3.1 | 2.1 | 0.9 | 6.8 | 6 |

TABLE 6

| | Excipient | Compression force [kgf] | Tablet weight [mg] | CV of tablet weight [%] | Breaking strength [kgf] | Disintegration time [sec] |
|---|---|---|---|---|---|---|
| Application Example Nos. | | | | | | |
| 6 | N | 500 | 201.0 | 0.7 | 3.4 | 42 |
| | | 1000 | 200.5 | 0.6 | 6.3 | 115 |
| | | 1500 | 200.4 | 0.8 | 8.4 | 197 |
| | | 2000 | 200.1 | 0.6 | 9.1 | 230 |
| 7 | O | 500 | 200.2 | 1.0 | 3.0 | 28 |
| | | 1000 | 199.7 | 0.5 | 6.0 | 84 |
| | | 1500 | 200.4 | 0.7 | 7.9 | 147 |
| | | 2000 | 200.0 | 0.4 | 8.7 | 193 |
| Comparative Application Example Nos. | | | | | | |
| 8 | F | 500 | 199.8 | 1.8 | 3.6 | 129 |
| | | 1000 | 199.6 | 2.1 | 6.4 | 290 |
| | | 1500 | 200.2 | 2.0 | 8.5 | 409 |
| | | 2000 | 201.3 | 1.8 | 9.4 | 516 |
| 9 | P | 500 | 200.3 | 1.6 | 1.3 | 13 |
| | | 1000 | 200.6 | 1.3 | 2.4 | 19 |
| | | 1500 | 200.1 | 1.5 | 3.2 | 25 |
| | | 2000 | 200.2 | 1.3 | 3.7 | 28 |
| 10 | Q | 500 | 201.1 | 0.8 | 1.6 | 9 |
| | | 1000 | 200.7 | 0.8 | 3.4 | 17 |
| | | 1500 | 200.2 | 0.7 | 4.3 | 27 |
| | | 2000 | 200.6 | 0.9 | 4.7 | 29 |
| 11 | R | 500 | 199.3 | 0.7 | 1.1 | 5 |
| | | 1000 | 200.6 | 0.6 | 2.1 | 7 |
| | | 1500 | 200.4 | 0.7 | 2.8 | 9 |
| | | 2000 | 200.2 | 0.7 | 3.3 | 11 |
| 12 | S | 500 | 199.3 | 0.9 | 1.6 | 10 |
| | | 1000 | 200.6 | 0.9 | 3.3 | 16 |
| | | 1500 | 200.4 | 0.8 | 4.2 | 22 |
| | | 2000 | 200.2 | 0.7 | 4.5 | 28 |

TABLE 7 (A)

Respective specific volumes $V_p$ (cm$^3$/g) of ten tablets of excipient A

| Tablet Nos. | Compression pressure P (kgf/cm$^2$) | | | | |
|---|---|---|---|---|---|
| | 200 | 400 | 800 | 1200 | 1600 |
| 1 | 0.846 | 0.721 | 0.651 | 0.627 | 0.620 |
| 2 | 0.849 | 0.716 | 0.648 | 0.625 | 0.619 |
| 3 | 0.847 | 0.722 | 0.653 | 0.631 | 0.616 |
| 4 | 0.852 | 0.719 | 0.653 | 0.628 | 0.614 |
| 5 | 0.844 | 0.716 | 0.651 | 0.633 | 0.621 |
| 6 | 0.851 | 0.717 | 0.650 | 0.632 | 0.617 |
| 7 | 0.847 | 0.719 | 0.654 | 0.628 | 0.620 |
| 8 | 0.851 | 0.720 | 0.656 | 0.628 | 0.619 |
| 9 | 0.848 | 0.721 | 0.651 | 0.631 | 0.617 |
| 10 | 0.844 | 0.722 | 0.653 | 0.630 | 0.616 |

TABLE 7 (B)

Respective specific volumes $V_p$ (cm$^3$/g) of ten tablets of excipient B

| Tablet Nos. | Compression pressure P (kgf/cm$^2$) | | | | |
|---|---|---|---|---|---|
| | 200 | 400 | 800 | 1200 | 1600 |
| 1 | 1.032 | 0.863 | 0.770 | 0.743 | 0.724 |
| 2 | 1.029 | 0.859 | 0.779 | 0.741 | 0.722 |
| 3 | 1.031 | 0.866 | 0.776 | 0.742 | 0.731 |
| 4 | 1.028 | 0.865 | 0.776 | 0.744 | 0.732 |
| 5 | 1.034 | 0.859 | 0.772 | 0.742 | 0.727 |
| 6 | 1.032 | 0.861 | 0.774 | 0.739 | 0.727 |
| 7 | 1.030 | 0.863 | 0.771 | 0.740 | 0.729 |
| 8 | 1.031 | 0.868 | 0.777 | 0.742 | 0.732 |
| 9 | 1.030 | 0.867 | 0.776 | 0.746 | 0.730 |
| 10 | 1.032 | 0.865 | 0.775 | 0.738 | 0.733 |

TABLE 7 (C)

Respective specific volumes $V_p$ (cm$^3$/g) of ten tablets of excipient C

| Tablet Nos. | Compression pressure P (kgf/cm$^2$) | | | | |
|---|---|---|---|---|---|
| | 200 | 400 | 800 | 1200 | 1600 |
| 1 | 1.062 | 0.891 | 0.796 | 0.770 | 0.746 |
| 2 | 1.064 | 0.889 | 0.799 | 0.771 | 0.751 |
| 3 | 1.066 | 0.891 | 0.798 | 0.772 | 0.753 |
| 4 | 1.059 | 0.893 | 0.802 | 0.765 | 0.759 |
| 5 | 1.056 | 0.887 | 0.797 | 0.765 | 0.751 |
| 6 | 1.062 | 0.886 | 0.799 | 0.767 | 0.752 |
| 7 | 1.057 | 0.891 | 0.801 | 0.770 | 0.753 |
| 8 | 1.062 | 0.893 | 0.797 | 0.769 | 0.751 |

TABLE 7 (C)-continued

Respective specific volumes $V_p$ (cm³/g) of ten tablets of excipient C

| Tablet Nos. | Compression pressure P (kgf/cm²) | | | | |
|---|---|---|---|---|---|
| | 200 | 400 | 800 | 1200 | 1600 |
| 9 | 1.059 | 0.882 | 0.802 | 0.763 | 0.750 |
| 10 | 1.064 | 0.888 | 0.797 | 0.766 | 0.749 |

TABLE 7 (D)

Respective specific volumes $V_p$ (cm³/g) of ten tablets of excipient D

| Tablet Nos. | Compression pressure P (kgf/cm²) | | | | |
|---|---|---|---|---|---|
| | 200 | 400 | 800 | 1200 | 1600 |
| 1 | 0.714 | 0.601 | 0.540 | 0.524 | 0.511 |
| 2 | 0.715 | 0.602 | 0.541 | 0.523 | 0.512 |
| 3 | 0.712 | 0.604 | 0.537 | 0.522 | 0.509 |
| 4 | 0.714 | 0.602 | 0.542 | 0.515 | 0.510 |
| 5 | 0.712 | 0.600 | 0.541 | 0.516 | 0.507 |
| 6 | 0.710 | 0.599 | 0.543 | 0.522 | 0.508 |
| 7 | 0.713 | 0.599 | 0.545 | 0.523 | 0.509 |
| 8 | 0.714 | 0.596 | 0.539 | 0.516 | 0.508 |
| 9 | 0.714 | 0.603 | 0.539 | 0.519 | 0.506 |
| 10 | 0.711 | 0.600 | 0.537 | 0.517 | 0.511 |

TABLE 7 (E)

Respective specific volumes $V_p$ (cm³/g) of ten tablets of excipient E

| Tablet Nos. | Compression pressure P (kgf/cm²) | | | | |
|---|---|---|---|---|---|
| | 200 | 400 | 800 | 1200 | 1600 |
| 1 | 0.973 | 0.825 | 0.747 | 0.722 | 0.710 |
| 2 | 0.977 | 0.829 | 0.750 | 0.725 | 0.709 |
| 3 | 0.970 | 0.830 | 0.745 | 0.718 | 0.708 |
| 4 | 0.971 | 0.829 | 0.748 | 0.719 | 0.706 |
| 5 | 0.969 | 0.825 | 0.747 | 0.720 | 0.705 |
| 6 | 0.972 | 0.826 | 0.746 | 0.719 | 0.707 |
| 7 | 0.974 | 0.824 | 0.752 | 0.724 | 0.711 |
| 8 | 0.973 | 0.825 | 0.751 | 0.721 | 0.709 |
| 9 | 0.972 | 0.824 | 0.749 | 0.722 | 0.707 |
| 10 | 0.976 | 0.827 | 0.748 | 0.724 | 0.706 |

TABLE 7 (F)

Respective specific volumes $V_p$ (cm³/g) of ten tablets of excipient F

| Tablet Nos. | Compression pressure P (kgf/cm²) | | | | |
|---|---|---|---|---|---|
| | 200 | 400 | 800 | 1200 | 1600 |
| 1 | 0.824 | 0.694 | 0.630 | 0.607 | 0.596 |
| 2 | 0.823 | 0.693 | 0.628 | 0.608 | 0.595 |
| 3 | 0.823 | 0.697 | 0.627 | 0.607 | 0.596 |
| 4 | 0.822 | 0.696 | 0.629 | 0.606 | 0.598 |
| 5 | 0.822 | 0.695 | 0.630 | 0.608 | 0.597 |
| 6 | 0.821 | 0.693 | 0.634 | 0.608 | 0.597 |
| 7 | 0.820 | 0.694 | 0.631 | 0.610 | 0.596 |
| 8 | 0.821 | 0.693 | 0.631 | 0.609 | 0.598 |
| 9 | 0.819 | 0.698 | 0.630 | 0.607 | 0.597 |
| 10 | 0.820 | 0.700 | 0.629 | 0.609 | 0.598 |

TABLE 7 (G)

Respective specific volumes $V_p$ (cm³/g) of ten tablets of excipient G

| Tablet Nos. | Compression pressure P (kgf/cm²) | | | | |
|---|---|---|---|---|---|
| | 200 | 400 | 800 | 1200 | 1600 |
| 1 | 1.013 | 0.869 | 0.788 | 0.756 | 0.741 |
| 2 | 1.010 | 0.870 | 0.785 | 0.757 | 0.742 |
| 3 | 1.015 | 0.871 | 0.785 | 0.763 | 0.743 |
| 4 | 1.014 | 0.870 | 0.789 | 0.760 | 0.746 |
| 5 | 1.013 | 0.869 | 0.790 | 0.760 | 0.745 |
| 6 | 1.014 | 0.870 | 0.787 | 0.758 | 0.744 |
| 7 | 1.013 | 0.865 | 0.788 | 0.757 | 0.751 |
| 8 | 1.015 | 0.867 | 0.789 | 0.761 | 0.745 |
| 9 | 1.015 | 0.865 | 0.786 | 0.760 | 0.744 |
| 10 | 1.016 | 0.866 | 0.787 | 0.760 | 0.747 |

TABLE 7 (H)

Respective specific volumes $V_p$ (cm³/g) of ten tablets of excipient H

| Tablet Nos. | Compression pressure P (kgf/cm²) | | | | |
|---|---|---|---|---|---|
| | 200 | 400 | 800 | 1200 | 1600 |
| 1 | 1.062 | 0.902 | 0.820 | 0.787 | 0.775 |
| 2 | 1.061 | 0.904 | 0.817 | 0.789 | 0.776 |
| 3 | 1.058 | 0.900 | 0.816 | 0.792 | 0.778 |
| 4 | 1.060 | 0.899 | 0.820 | 0.787 | 0.773 |
| 5 | 1.061 | 0.903 | 0.818 | 0.790 | 0.773 |
| 6 | 1.062 | 0.901 | 0.816 | 0.789 | 0.775 |
| 7 | 1.060 | 0.902 | 0.817 | 0.791 | 0.776 |
| 8 | 1.059 | 0.900 | 0.818 | 0.789 | 0.772 |
| 9 | 1.061 | 0.901 | 0.819 | 0.791 | 0.777 |
| 10 | 1.060 | 0.902 | 0.818 | 0.790 | 0.776 |

TABLE 7 (I)

Respective specific volumes $V_p$ (cm³/g) of ten tablets of excipient I

| Tablet Nos. | Compression pressure P (kgf/cm²) | | | | |
|---|---|---|---|---|---|
| | 200 | 400 | 800 | 1200 | 1600 |
| 1 | 1.055 | 0.890 | 0.793 | 0.765 | 0.749 |
| 2 | 1.053 | 0.881 | 0.797 | 0.763 | 0.751 |
| 3 | 1.059 | 0.889 | 0.800 | 0.765 | 0.748 |
| 4 | 1.055 | 0.887 | 0.795 | 0.765 | 0.747 |
| 5 | 1.054 | 0.886 | 0.794 | 0.765 | 0.751 |
| 6 | 1.057 | 0.885 | 0.797 | 0.766 | 0.750 |
| 7 | 1.056 | 0.886 | 0.799 | 0.761 | 0.750 |
| 8 | 1.056 | 0.887 | 0.795 | 0.769 | 0.752 |
| 9 | 1.056 | 0.884 | 0.796 | 0.767 | 0.748 |
| 10 | 1.060 | 0.888 | 0.795 | 0.766 | 0.749 |

TABLE 7 (J)

Respective specific volumes $V_p$ (cm³/g) of ten tablets of excipient J

| Tablet Nos. | Compression pressure P (kgf/cm²) | | | | |
|---|---|---|---|---|---|
| | 200 | 400 | 800 | 1200 | 1600 |
| 1 | 1.825 | 1.537 | 1.369 | 1.314 | 1.281 |
| 2 | 1.824 | 1.533 | 1.371 | 1.313 | 1.280 |
| 3 | 1.829 | 1.537 | 1.366 | 1.310 | 1.279 |
| 4 | 1.827 | 1.536 | 1.370 | 1.313 | 1.280 |
| 5 | 1.826 | 1.540 | 1.369 | 1.311 | 1.277 |
| 6 | 1.826 | 1.531 | 1.366 | 1.309 | 1.279 |
| 7 | 1.824 | 1.539 | 1.371 | 1.310 | 1.277 |

TABLE 7 (J)-continued

Respective specific volumes $V_p$ (cm³/g) of ten tablets of excipient J

| Tablet Nos. | Compression pressure P (kgf/cm²) | | | | |
|---|---|---|---|---|---|
| | 200 | 400 | 800 | 1200 | 1600 |
| 8 | 1.825 | 1.537 | 1.370 | 1.308 | 1.284 |
| 9 | 1.829 | 1.538 | 1.373 | 1.309 | 1.281 |
| 10 | 1.827 | 1.534 | 1.372 | 1.307 | 1.283 |

TABLE 7 (K)

Respective specific volumes $V_p$ (cm³/g) of ten tablets of excipient K

| Tablet Nos. | Compression pressure P (kgf/cm²) | | | | |
|---|---|---|---|---|---|
| | 200 | 400 | 800 | 1200 | 1600 |
| 1 | 0.922 | 0.788 | 0.711 | 0.681 | 0.671 |
| 2 | 0.921 | 0.787 | 0.712 | 0.688 | 0.673 |
| 3 | 0.924 | 0.785 | 0.713 | 0.685 | 0.672 |
| 4 | 0.921 | 0.788 | 0.709 | 0.684 | 0.668 |
| 5 | 0.916 | 0.788 | 0.712 | 0.683 | 0.673 |
| 6 | 0.920 | 0.789 | 0.710 | 0.684 | 0.670 |
| 7 | 0.921 | 0.790 | 0.711 | 0.685 | 0.673 |
| 8 | 0.919 | 0.786 | 0.716 | 0.688 | 0.672 |
| 9 | 0.918 | 0.789 | 0.715 | 0.686 | 0.670 |
| 10 | 0.920 | 0.791 | 0.712 | 0.686 | 0.669 |

TABLE 7 (L)

Respective specific volumes $V_p$ (cm³/g) of ten tablets of excipient L

| Tablet Nos. | Compression pressure P (kgf/cm²) | | | | |
|---|---|---|---|---|---|
| | 200 | 400 | 800 | 1200 | 1600 |
| 1 | 2.050 | 1.439 | 1.051 | 0.913 | 0.838 |
| 2 | 2.057 | 1.442 | 1.057 | 0.913 | 0.832 |
| 3 | 2.049 | 1.441 | 1.055 | 0.911 | 0.834 |
| 4 | 2.054 | 1.443 | 1.053 | 0.912 | 0.836 |
| 5 | 2.051 | 1.441 | 1.056 | 0.910 | 0.837 |
| 6 | 2.052 | 1.441 | 1.054 | 0.909 | 0.835 |
| 7 | 2.053 | 1.443 | 1.056 | 0.907 | 0.836 |
| 8 | 2.058 | 1.439 | 1.054 | 0.911 | 0.835 |
| 9 | 2.056 | 1.437 | 1.056 | 0.910 | 0.837 |
| 10 | 2.050 | 1.440 | 1.055 | 0.913 | 0.837 |

TABLE 7 (M)

Respective specific volumes $V_p$ (cm³/g) of ten tablets of excipient M

| Tablet Nos. | Compression pressure P (kgf/cm²) | | | | |
|---|---|---|---|---|---|
| | 200 | 400 | 800 | 1200 | 1600 |
| 1 | 0.887 | 0.755 | 0.677 | 0.657 | 0.643 |
| 2 | 0.886 | 0.754 | 0.682 | 0.653 | 0.640 |
| 3 | 0.889 | 0.755 | 0.680 | 0.656 | 0.641 |
| 4 | 0.891 | 0.753 | 0.682 | 0.652 | 0.638 |
| 5 | 0.890 | 0.754 | 0.680 | 0.655 | 0.639 |
| 6 | 0.888 | 0.755 | 0.678 | 0.654 | 0.640 |
| 7 | 0.887 | 0.757 | 0.679 | 0.655 | 0.644 |
| 8 | 0.888 | 0.753 | 0.680 | 0.655 | 0.642 |
| 9 | 0.889 | 0.755 | 0.679 | 0.652 | 0.641 |
| 10 | 0.890 | 0.750 | 0.681 | 0.650 | 0.640 |

TABLE 7 (N)

Respective specific volumes $V_p$ (cm³/g) of ten tablets of excipient N

| Tablet Nos. | Compression pressure P (kgf/cm²) | | | | |
|---|---|---|---|---|---|
| | 200 | 400 | 800 | 1200 | 1600 |
| 1 | 0.959 | 0.792 | 0.705 | 0.673 | 0.658 |
| 2 | 0.960 | 0.796 | 0.704 | 0.675 | 0.659 |
| 3 | 0.960 | 0.793 | 0.703 | 0.670 | 0.656 |
| 4 | 0.959 | 0.792 | 0.703 | 0.674 | 0.657 |
| 5 | 0.963 | 0.793 | 0.701 | 0.672 | 0.659 |
| 6 | 0.961 | 0.790 | 0.699 | 0.673 | 0.655 |
| 7 | 0.962 | 0.794 | 0.704 | 0.672 | 0.657 |
| 8 | 0.961 | 0.794 | 0.702 | 0.672 | 0.657 |
| 9 | 0.960 | 0.795 | 0.708 | 0.671 | 0.654 |
| 10 | 0.961 | 0.788 | 0.703 | 0.673 | 0.657 |

TABLE 7 (O)

Respective specific volumes $V_p$ (cm³/g) of ten tablets of excipient O

| Tablet Nos. | Compression pressure P (kgf/cm²) | | | | |
|---|---|---|---|---|---|
| | 200 | 400 | 800 | 1200 | 1600 |
| 1 | 0.918 | 0.770 | 0.684 | 0.661 | 0.642 |
| 2 | 0.919 | 0.769 | 0.688 | 0.660 | 0.648 |
| 3 | 0.922 | 0.768 | 0.683 | 0.658 | 0.650 |
| 4 | 0.919 | 0.769 | 0.691 | 0.657 | 0.646 |
| 5 | 0.920 | 0.767 | 0.690 | 0.659 | 0.643 |
| 6 | 0.920 | 0.771 | 0.687 | 0.661 | 0.644 |
| 7 | 0.919 | 0.766 | 0.690 | 0.663 | 0.646 |
| 8 | 0.918 | 0.769 | 0.689 | 0.662 | 0.645 |
| 9 | 0.918 | 0.769 | 0.687 | 0.660 | 0.645 |
| 10 | 0.916 | 0.765 | 0.686 | 0.656 | 0.647 |

TABLE 7 (P)

Respective specific volumes $V_p$ (cm³/g) of ten tablets of excipient P

| Tablet Nos. | Compression pressure P (kgf/cm²) | | | | |
|---|---|---|---|---|---|
| | 200 | 400 | 800 | 1200 | 1600 |
| 1 | 1.871 | 1.580 | 1.410 | 1.351 | 1.323 |
| 2 | 1.877 | 1.578 | 1.413 | 1.352 | 1.322 |
| 3 | 1.875 | 1.579 | 1.411 | 1.357 | 1.323 |
| 4 | 1.876 | 1.580 | 1.417 | 1.355 | 1.328 |
| 5 | 1.877 | 1.581 | 1.415 | 1.354 | 1.325 |
| 6 | 1.872 | 1.581 | 1.411 | 1.356 | 1.324 |
| 7 | 1.874 | 1.580 | 1.414 | 1.358 | 1.327 |
| 8 | 1.875 | 1.579 | 1.413 | 1.355 | 1.326 |
| 9 | 1.875 | 1.577 | 1.413 | 1.352 | 1.326 |
| 10 | 1.876 | 1.580 | 1.415 | 1.355 | 1.321 |

TABLE 7 (Q)

Respective specific volumes $V_p$ (cm³/g) of ten tablets of excipient Q

| Tablet Nos. | Compression pressure P (kgf/cm²) | | | | |
|---|---|---|---|---|---|
| | 200 | 400 | 800 | 1200 | 1600 |
| 1 | 0.988 | 0.829 | 0.740 | 0.713 | 0.695 |
| 2 | 0.989 | 0.830 | 0.746 | 0.712 | 0.700 |
| 3 | 0.985 | 0.829 | 0.744 | 0.710 | 0.699 |
| 4 | 0.986 | 0.830 | 0.742 | 0.714 | 0.696 |
| 5 | 0.985 | 0.831 | 0.743 | 0.712 | 0.696 |
| 6 | 0.986 | 0.832 | 0.743 | 0.713 | 0.699 |
| 7 | 0.983 | 0.830 | 0.745 | 0.710 | 0.698 |

TABLE 7 (Q)-continued

Respective specific volumes $V_p$ (cm³/g) of ten tablets of excipient Q

| Tablet Nos. | Compression pressure P (kgf/cm²) | | | | |
|---|---|---|---|---|---|
| | 200 | 400 | 800 | 1200 | 1600 |
| 8 | 0.987 | 0.829 | 0.743 | 0.713 | 0.696 |
| 9 | 0.986 | 0.827 | 0.741 | 0.716 | 0.694 |
| 10 | 0.985 | 0.830 | 0.742 | 0.713 | 0.698 |

TABLE 7 (R)

Respective specific volumes $V_p$ (cm³/g) of ten tablets of excipient R

| Tablet Nos. | Compression pressure P (kgf/cm²) | | | | |
|---|---|---|---|---|---|
| | 200 | 400 | 800 | 1200 | 1600 |
| 1 | 0.984 | 0.836 | 0.745 | 0.713 | 0.697 |
| 2 | 0.980 | 0.831 | 0.747 | 0.715 | 0.696 |
| 3 | 0.987 | 0.833 | 0.748 | 0.714 | 0.701 |
| 4 | 0.984 | 0.834 | 0.749 | 0.715 | 0.696 |
| 5 | 0.985 | 0.835 | 0.743 | 0.712 | 0.699 |
| 6 | 0.980 | 0.834 | 0.744 | 0.716 | 0.702 |
| 7 | 0.983 | 0.837 | 0.746 | 0.717 | 0.698 |
| 8 | 0.982 | 0.836 | 0.745 | 0.718 | 0.700 |
| 9 | 0.985 | 0.830 | 0.746 | 0.714 | 0.697 |
| 10 | 0.986 | 0.830 | 0.747 | 0.712 | 0.698 |

TABLE 7 (S)

Respective specific volumes $V_p$ (cm³/g) of ten tablets of excipient S

| Tablet Nos. | Compression pressure P (kgf/cm²) | | | | |
|---|---|---|---|---|---|
| | 200 | 400 | 800 | 1200 | 1600 |
| 1 | 0.994 | 0.836 | 0.745 | 0.713 | 0.697 |
| 2 | 0.999 | 0.835 | 0.746 | 0.714 | 0.696 |
| 3 | 0.996 | 0.833 | 0.748 | 0.714 | 0.695 |
| 4 | 0.996 | 0.835 | 0.747 | 0.715 | 0.696 |
| 5 | 0.995 | 0.838 | 0.743 | 0.712 | 0.699 |
| 6 | 0.996 | 0.834 | 0.744 | 0.711 | 0.700 |
| 7 | 0.994 | 0.837 | 0.743 | 0.716 | 0.698 |
| 8 | 0.996 | 0.836 | 0.745 | 0.715 | 0.700 |
| 9 | 0.997 | 0.835 | 0.746 | 0.714 | 0.697 |
| 10 | 0.999 | 0.834 | 0.747 | 0.713 | 0.698 |

What is claimed is:

1. An excipient having high compactability, comprising white powdery microcrystalline cellulose obtained by subjecting a cellulosic material to hydrolysis with acid or oxidative degradation with alkali, said microcrystalline cellulose having an average degree of polymerization of from 100 to 375 and an acetic acid holding capacity of 280% or more, and having a compression characteristic satisfying an equality of formula (1):

$$P \cdot \frac{V_o}{V_o - V_p} = \frac{1}{a \cdot b} + \frac{P}{a} \quad (1)$$

wherein a is from 0.85 to 0.90, b is from 0.05 to 0.10, P represents the compression pressure (kgf/cm²) applied to said microcrystalline cellulose, $V_o$ represents the apparent specific volume (cm³/g) of said microcrystalline cellulose, and $V_p$ represents the specific volume (cm³/g) of said microcrystalline cellulose at said compression pressure P, wherein said white powdery microcrystalline cellulose has an apparent specific volume of from 4.0 to 6.0 cm³/q, a tapping apparent specific volume of 2.4 cm³/q or more and a specific surface area of less than 20 m²/g, and a content of particles having a diameter of 355 μm or more of 5% by weight or less, and has an average particle diameter of from 30 to 120 μm, and wherein said white powdery microcrystalline cellulose is further characterized such that when 500 mg of said microcrystalline cellulose is compressed at 100 kqf/cm² for 10 seconds to form a cylindrical tablet having a circular cross-sectional area of 1 cm², said tablet has a breaking strength of 10 kqf or more in a diametric direction thereof, and exhibits a disintegration time of 100 seconds or less, and wherein said acetic acid holding capacity means the amount of acetic acid which can be held by the pores of the powdery microcrystalline cellulose when the powdery microcrystalline cellulose is equilibrated with acetic acid, and is expressed in a weight percentage of the acetic acid which can be held by the microcrystalline cellulose, relative to the weight of the microcrystalline cellulose in a dry state, and wherein said tapping apparent specific volume is measured by a method in which a glass cylinder containing the white powdery microcrystalline cellulose lightly packed therein is subjected to tapping onto a stand made of a relatively soft material from a height of several centimeters in an approximately vertical direction until the packing density of the white powdery microcrystalline cellulose is not increased by tapping any more, and the volume of the resultant white powdery microcrystalline cellulose is measured and divided by the weight of the white powdery microcrystalline cellulose.

2. The excipient according to claim 1, wherein the average degree of polymerization of said white powdery microcrystalline cellulose is from 180 to 220.

3. The excipient according to claim 1, wherein said cylindrical tablet has a breaking strength of 11 kgf or more in a diametric direction thereof.

4. The excipient according to any one of claims 1, 2 and 3, wherein said microcrystalline cellulose is further characterized such that when said microcrystalline cellulose has a water content of from 5 to 6% by weight, the microcrystalline cellulose has a transverse relaxation time of 0.00024 second or less with respect to said water, as measured by NMR spectroscopic analysis.

5. A process for preparing the excipient according to claim 1, which comprises subjecting a cellulosic material to hydrolysis with acid, or oxidative degradation with alkali to form cellulose particles, subjecting said cellulose particles to purification to obtain aqueous purified cellulose particles, adjusting the water content of said aqueous purified cellulose particles to obtain an aqueous dispersion of the purified cellulose particles, wherein said aqueous dispersion has a solids content of 40% or less by weight, a pH value of from 5 to 8.5 and an electrical conductivity of 300 μs/cm or less, and subjecting said aqueous dispersion to heat treatment at 100° C. or more, followed by drying, thereby obtaining a microcrystalline cellulose.

6. The process according to claim 5, wherein said aqueous dispersion of the purified cellulose particles has a solids content of from 5 to 23% by weight.

7. The process according to claim 5 or 6, wherein said heat treatment and said drying are performed by means of a drum dryer or a belt dryer.

8. The process according to claim 5 or 6, wherein said microcrystalline cellulose is subjected to pulverizing and sieving to adjust the particle size distribution thereof.

9. A process for preparing the excipient according to claim 1, which comprises subjecting a cellulosic material to hydrolysis with acid or oxidative degradation with alkali to form cellulose particles, subjecting said cellulose particles to purification to obtain aqueous purified cellulose particles, adjusting the water content of said aqueous purified cellulose particles to obtain an aqueous dispersion of the purified cellulose particles, wherein said aqueous dispersion has a solids content of 23% or less by weight, a pH value of from 5 to 8.5 and an electrical conductivity of 300 μs/cm or less, and spreading said aqueous dispersion on a substrate to obtain a film of said aqueous dispersion, followed by drying, thereby obtaining a microcrystalline cellulose.

10. The process according to claim 9, wherein said drying is performed by means of a drum dryer or a belt dryer.

11. The process according to claim 9, wherein said microcrystalline cellulose is subjected to pulverizing and sieving to adjust the particle size distribution thereof.

* * * * *